United States Patent
Deftereos et al.

(10) Patent No.: US 9,763,939 B2
(45) Date of Patent: Sep. 19, 2017

(54) COMPOSITIONS AND METHODS FOR TREATING MITOCHONDRIAL DISEASES

(71) Applicant: BIOVISTA, INC., Charlottesville, VA (US)

(72) Inventors: Spyros Deftereos, Athens (GR); Andreas Persidis, Athens (GR)

(73) Assignee: BIOVISTA, INC., Charlottesville, VA (US)

( * ) Notice: Subject to any disclaimer, the term of this patent is extended or adjusted under 35 U.S.C. 154(b) by 0 days.

(21) Appl. No.: 14/924,986

(22) Filed: Oct. 28, 2015

(65) Prior Publication Data

US 2016/0213667 A1 Jul. 28, 2016

Related U.S. Application Data

(63) Continuation of application No. 14/381,126, filed as application No. PCT/US2013/027722 on Feb. 26, 2013, now abandoned.

(60) Provisional application No. 61/603,763, filed on Feb. 27, 2012.

(51) Int. Cl.

| | | |
|---|---|---|
| *A61K 31/4985* | (2006.01) | |
| *A61K 31/122* | (2006.01) | |
| *A61K 31/355* | (2006.01) | |
| *A61K 31/375* | (2006.01) | |
| *A61K 31/385* | (2006.01) | |
| *A61K 31/51* | (2006.01) | |
| *C07D 471/16* | (2006.01) | |
| *C07D 487/06* | (2006.01) | |
| *A61K 9/20* | (2006.01) | |

(52) U.S. Cl.
CPC ........ *A61K 31/4985* (2013.01); *A61K 9/2013* (2013.01); *A61K 31/122* (2013.01); *A61K 31/355* (2013.01); *A61K 31/375* (2013.01); *A61K 31/385* (2013.01); *A61K 31/51* (2013.01); *C07D 471/16* (2013.01); *C07D 487/06* (2013.01)

(58) Field of Classification Search
CPC .................................................. C07D 487/06
USPC ......................................................... 514/250
See application file for complete search history.

(56) References Cited

U.S. PATENT DOCUMENTS

2011/0111014 A1* 5/2011 Langston ............... A61K 38/29
424/450

* cited by examiner

*Primary Examiner* — Taofiq A Solola
(74) *Attorney, Agent, or Firm* — Brannon Sowers & Cracraft PC

(57) ABSTRACT

The invention described herein relates to methods for treating mitochondrial diseases. In particular, the invention relates to methods for treating mitochondrial diseases by administering therapeutically effective amounts of one or more tetracyclic pyrazinoindoles, and/or pharmaceutically acceptable salts thereof.

16 Claims, 4 Drawing Sheets

Apoptosis

Viability

COMPOSITIONS AND METHODS FOR TREATING MITOCHONDRIAL DISEASES

CROSS-REFERENCE TO RELATED APPLICATIONS

This application is a continuation of U.S. patent application Ser. No. 14/381,126, filed Aug. 26, 2014, which is a U.S. national application under 37 C.F.R. §371(b) of International Application Serial No. PCT/US2013/027722 filed Feb. 26, 2013, which claims priority under 35 U.S.C. §119(e) to U.S. Provisional Application No. 61/603,763, filed on Feb. 27, 2012, the entire disclosures of which are incorporated herein by reference.

TECHNICAL FIELD

The invention described herein relates to methods for treating mitochondrial diseases. In particular, the invention relates to methods for treating mitochondrial diseases by administering therapeutically effective amounts of one or more tetracyclic pyrazinoindoles, and/or pharmaceutically acceptable salts thereof.

BACKGROUND AND SUMMARY OF THE INVENTION

Mitochondrial diseases are a group of disorders caused by dysfunctional mitochondria, the organelles that are the "powerhouses" in cells. Mitochondria are found in every cell of the body except red blood cells. Mitochondria convert the energy of food molecules into the ATP that powers most cell functions. Mitochondrial diseases are often caused by genetics or mutations to the mitochondrial DNA that affect mitochondria function. Mitochondrial diseases take on unique characteristics both because of the way the diseases are often inherited and because mitochondria are so critical to cell function. Mitochondrial diseases elicit in a variety of organs, and with a variety of symptoms, some of which are directly caused by the dysfunction, and others which are the downstream consequences of the dysfunction. For example, the subclass of these diseases that have neuromuscular disease symptoms are often called a mitochondrial myopathy. There is evidence that mitochondrial dysfunction may be a molecular basis of bipolar disorder. In addition, classical mitochondrial diseases occur in a subset of individuals with autism and may be caused by genetic anomalies or mitochondrial respiratory pathway deficits.

The clinical presentation of the mitochondrial disease include poor growth, loss of muscle coordination, muscle weakness, visual problems, hearing problems, learning disabilities, heart disease, liver disease, kidney disease, gastrointestinal disorders, respiratory disorders, neurological problems, autonomic dysfunction, and dementia.

Illustrative mitochondrial diseases and myopathies include Leber's hereditary optic neuropathy (LHON). LHON results in visual loss beginning in young adulthood, eye disorder characterized by progressive loss of central vision due to degeneration of the optic nerves and retina, Wolff-Parkinson-White syndrome, a manifestation of LHON showing as a cardiac condition and/or arrhythmia that is believed herein to be caused by a dysfunctional circuit in the heart conduction. LHON reportedly affects 1 in 50,000 people in Finland.

Illustrative mitochondrial diseases and myopathies include diabetes mellitus and deafness (DAD). DAD is a combination of symptoms that appears at an early age and is believed herein to be caused at least in part by mitochondrial disease. Without being bound by theory, it is believed herein that DAD is a specific manifestation of symptoms resulting from mitochondrial starving of the pancreas, which then leads to a diabetic condition, and accompanying deafness. DAD is not believed herein to be a an autoimmune disease, but rather a particular combination of symptoms that arise from mitochondrial dysfunction.

Illustrative mitochondrial diseases and myopathies include Leigh's disease or Leigh syndrome, a subacute sclerosing encephalopathy. Leigh's disease elicits after normal development, then the disease usually begins late in the first year of life, although onset may occur in adulthood. A rapid decline in function occurs and is marked by seizures, altered states of consciousness, dementia, and ventilatory failure.

Illustrative mitochondrial diseases and myopathies include neuropathy, ataxia, retinitis pigmentosa, and ptosis (NARP). NARP is a disease identified as the progressive set of symptoms represented by the acronym, and may also include dementia.

Illustrative mitochondrial diseases and myopathies include Myoneurogenic gastrointestinal encephalopathy (MNGIE). MNGIE presents as a gastrointestinal pseudo-obstruction, and may lead to neuropathy.

Illustrative mitochondrial diseases and myopathies include Myoclonic Epilepsy with Ragged Red Fibers (MERRF). MERRF is a progressive myoclonic epilepsy that is believed herein to be caused at least in part by mitochondrial dysfunction. MERRF is associated with ragged red fibers, clumps of diseased mitochondria that accumulate in the subsarcolemmal region of the muscle fiber. The "ragged red fibers" are observed when muscle is stained with modified Gömöri trichrome stain. MERRF reportedly leads to short stature, hearing loss, lactic acidosis, and/or exercise intolerance.

Illustrative mitochondrial diseases and myopathies include Mitochondrial myopathy, encephalomyopathy, lactic acidosis, stroke-like symptoms (MELAS).

Mitochondrial diseases and myopathies that may be treated using the compositions and methods described herein include those diseases that are characterized mitochondrial dysfunction, and may be accompanied by high levels of oxidative stress. The diseases themselves may be genetic, arise from a primary mutation that causes a mitochondrial dysfunction, and/or which causes high oxidative stress. Mitochondrial diseases and myopathies that may be treated using the compositions and methods described herein if left untreated may cause tissue damage and/or further genetic damage, the latter arising from additional mutations and protein damage, leading to a cascade of problems.

Friedreich's ataxia (FRDA) is the most common of the inherited ataxias, and affects 1 in 50,000 people in general, and approximately 1.5 per 100,000 per year among Europeans and North Americans of European descent. Friedreich ataxia is a progressive disorder with significant morbidity. Loss of ambulation typically occurs 15 years after disease onset. More than 95% of surviving patients are wheelchair bound by age 45 years. The average age of death is reportedly 37.7 years (range, 21-69) (see, Harding et al. J Med Genet. August 1981; 18(4):285-7). FRDA is an autosomal recessively inherited progressive neurodegenerative disease that is characterized by progressive neurodegeneration, diabetes and life-threatening hypertrophic cardiomyopathy. Clinically, FRDA is characterized by multiple symptoms including progressive gait and limb ataxia, dysarthria, diabetes mellitus and hypertrophic cardiomyopathy (Sturm et al., *E. J. Clin. Invest.* 2005; 35:711-717).

Friedreich's ataxia is reportedly caused by a GAA-trinucleotide repeat expansion within intron 1 of the FXN gene (Campuzano et al., Friedreich's ataxia: autosomal recessive disease caused by an intronic GAA triplet repeat expansion *Science* 271:1423-1427 (1996)), which induces FXN gene silencing and hence reduced expression of the essential mitochondrial protein frataxin (Campuzano et al., Frataxin is reduced in Friedreich ataxia patients and is associated with mitochondrial membranes *Hum Mol Genet* 6:1771-1780 (1997)). The frataxin gene is located on chromosome locus 9q13. Without being bound by theory, due to the mitochondrial localization of frataxin, the neurological and cardiological degenerations observed in FRDA are believed herein to be the result of a mitochondrial defect. Although the exact physiological function of frataxin is unknown, without being bound by theory, it is believed herein that frataxin may be involved in mitochondrial iron homeostasis and/or assembly of iron-sulfur (FeS) proteins and heme synthesis. In particular, frataxin insufficiency reportedly leads to iron-sulfur cluster protein deficits, oxidative stress, mitochondrial iron accumulation and resultant cell death, with the primary site of pathology being in the large sensory neurons of the dorsal root ganglia (DRG) and the dentate nucleus of the cerebellum (Koeppen, Friedreich's ataxia: pathology, pathogenesis, and molecular genetics *J Neurol Sci* 303, 1-12 (2011)). Intramitochondrial iron accumulation has also been reported to possibly initiate the production of hydroxyl radicals, leading to inactivation of FeS enzymes, lipid peroxidation and damage to nucleic acids, and proteins. In addition, it has been reported that the outcome is progressive spinocerebellar neurodegeneration, diabetes and cardiomyopathy, with death commonly in early adulthood (Pandolfo, Friedreich ataxia: the clinical picture *J Neurol* 256 Suppl 1, 3-8 (2009)).

Despite remarkable progress in delineating the biochemical and genetic basis of mitochondrial disorders over the past 20 years, progress in establishing effective treatment has generally been limited. Many potential interventions have been proposed, most of which have not been demonstrated objectively to be beneficial (see, for example, DiMauro, Biochimica et Biophysica Acta 179:1159-1167 (2009))

Accordingly, compounds, compositions, and methods are needed for treating mitochondrial diseases, such as FRDA, LHON, DAD, Leigh's disease, NARP, MNGIE, MERRF, MELAS, and the like. It is believed herein that compounds that also exhibit antioxidant like behavior but which may be more than general antioxidants, or general oxidant scavengers, are useful in treating such mitochondrial diseases.

It has been discovered that tetracyclic pyrazinoindoles, and in particular, hydrogenated tetracyclic pyrazinoindoles, and pharmaceutically acceptable salts thereof, are useful in treating patients suffering from or in need of relief from FRDA, LHON, DAD, Leigh's disease, NARP, MNGIE, MERRF, MELAS, and like mitochondrial diseases. Without being bound by theory, it is believed herein that the compounds described herein protect, or directly protect, neuronal cells from the oxidative stress that accompanies FRDA, LHON, DAD, Leigh's disease, NARP, MNGIE, MERRF, MELAS, and like mitochondrial diseases. The use of tetracyclic pyrazinoindoles, or pharmaceutically acceptable salts thereof, in treating such mitochondrial diseases has heretofore been unknown.

In one illustrative embodiment of the invention described herein, methods are described for treating FRDA, LHON, DAD, Leigh's disease, NARP, MNGIE, MERRF, MELAS, and like mitochondrial diseases. In one aspect, the methods described herein include the step of administering a therapeutically effective amount of one or more tetracyclic pyrazinoindoles and/or pharmaceutically acceptable salts thereof to a patient suffering from, or in need of relief from one or more forms of FRDA, LHON, DAD, Leigh's disease, NARP, MNGIE, MERRF, MELAS, and like mitochondrial diseases. As used herein, FRDA, LHON, DAD, Leigh's disease, NARP, MNGIE, MERRF, MELAS, and like mitochondrial diseases include borderline forms of each of the foregoing. Borderline forms of such diseases include early forms of the diseases treatable herein, where diagnosis on the basis of symptoms may be difficult.

Illustrative compositions for use in the methods described herein include a therapeutically effective amount of one or more tetracyclic pyrazinoindoles and/or pharmaceutically acceptable salts thereof.

In another illustrative embodiment, the methods described herein include the step of co-administering a therapeutically effective amount of one or more tetracyclic pyrazinoindoles and/or pharmaceutically acceptable salts thereof, and a therapeutically effective amount of one or more other pharmaceutically effective agents. Illustrative other pharmaceutically effective agents include, but are not limited to, coenzyme Q10, and analogs and derivatives thereof, such as antioxidants, including idebenone, EPI-A0001, pioglitazone, ubiquinone, ubidecarenone, coenzyme Q, and the like, and/or pharmaceutically acceptable salts thereof, iron chelators, such as deferiprone, and the like, frataxin-increasing compounds, such as erythropoietin (EPO), and the like, histone deacetylase (HDAC) inhibitors, dimebolins, such as dimebon, and/or pharmaceutically acceptable salts thereof, certain vitamins, such as vitamin C, vitamin E, thiamine, and/or riboflavin, and/or pharmaceutically acceptable salts thereof, creatine, carnitine, and analogs and derivatives thereof, such as acetylcarnitine, acetyluridine, trolox, curcumin, alpha lipoic acid, dichloroacetate, pyruvate, and/or pharmaceutically acceptable salts of any of the foregoing.

In another embodiment, illustrative compositions include a therapeutically effective amount of one or more tetracyclic pyrazinoindoles and/or pharmaceutically acceptable salts thereof, and a therapeutically effective amount of another such pharmaceutically effective agent, such idebenone and/or pharmaceutically acceptable salts thereof. In another embodiment, the compositions include a therapeutically effective amount of one or more tetracyclic pyrazinoindoles and/or pharmaceutically acceptable salts thereof, and a therapeutically effective amount of trolox. In another embodiment, the compositions include a therapeutically effective amount of one or more tetracyclic pyrazinoindoles and/or pharmaceutically acceptable salts thereof, and a therapeutically effective amount of alpha-lipoic acid. In another embodiment, the compositions include a therapeutically effective amount of one or more tetracyclic pyrazinoindoles and/or pharmaceutically acceptable salts thereof, and a therapeutically effective amount of acetylcarnitine. It is to be understood that in each of the foregoing compositions, all combinations of compounds described herein may be included in the compositions, such as but not limited to a therapeutically effective amount of one or more tetracyclic pyrazinoindoles and/or pharmaceutically acceptable salts thereof, and a therapeutically effective amount of idebenone and/or pharmaceutically acceptable salts thereof, and a therapeutically effective amount of trolox to a patient.

In another illustrative embodiment, kits or packages are described herein. Illustrative kits and packages include instructions and preparations, where the co-administered compounds are placed in a format following the dosing protocol instructions, as described herein. For example, an illustrative package may include a grid pattern, wherein each section includes a dual or triple bubble pack for the one or more tetracyclic pyrazinoindole dosages, and illustratively one or more of the dimebolin dosage, idebenone dosage, trolox dosage, vitamin E dosage, the vitamin C dosage, and/or the CoQ10 dosage, and/or the acetylcarnitine dosage, and/or the carnitine dosage, and/or the acetyluridine dosage, and/or the curcumin dosage, and/or the dichloroacetate dosage, and/or the Pyruvate dosage, and/or the thiamine dosage, and/or the riboflavin dosage, and/or the Creatine dosage. It is appreciated that other configurations that include other combinations of one or more of the dimebolin dosage, CoQ10 dosage, idebenone dosage, the trolox dosage, the vitamin E dosage, the vitamin C dosage, the carnitine dosage, the acetylcarnitine dosage, the acetyluridine dosage, the curcumin dosage, the dichloroacetate dosage, the pyruvate dosage, the thiamine dosage, the riboflavin dosage, and/or the creatine dosage are described herein.

DETAILED DESCRIPTION

Figure 1A:
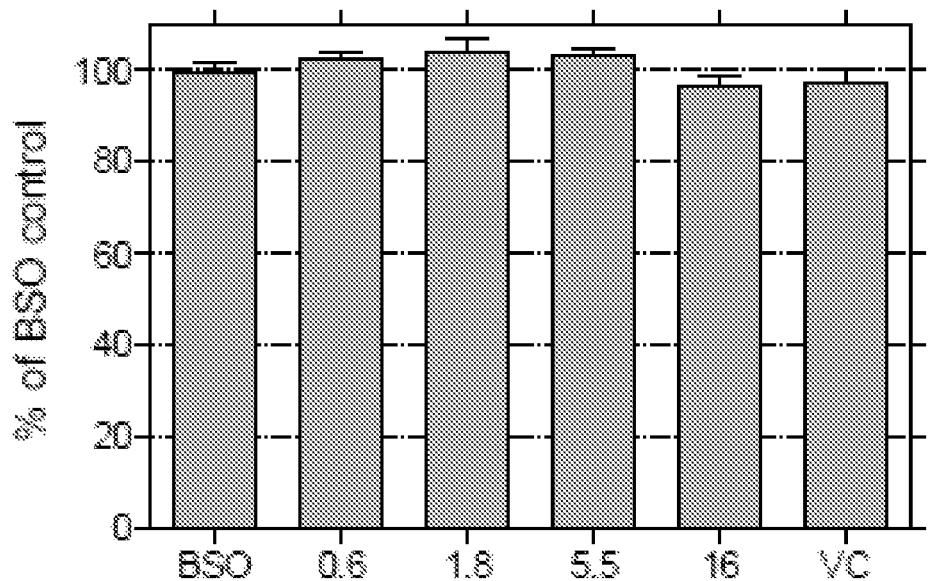
FIGS. 1A and 1B shows treatment with pirlindole of human primary fibroblasts from patients diagnosed with Friedreich's ataxia. Cell apoptosis and viability effects of pirlindole (addition 24 h before lesion) on FRDA cells as % of the buthionine-S,R-sulfoximine (BSO) lesion are shown. Statistical significance is indicated by NS=not significant $p>0.1$, $*=p<0.05$, $=p<0.01$, $*=p<0.001$ as determined by One-Way ANOVA. Data are shown as group mean+/−SEM.

Described herein are compositions and methods for treating mitochondrial diseases, Illustrative mitochondrial diseases include FRDA, LHON, DAD, Leigh's disease, NARP, MNGIE, MERRF, MELAS, and the like.

In one embodiment, the compositions and methods described herein include administering a therapeutically effective amount of one or more tetracyclic pyrazinoindoles and/or pharmaceutically acceptable salts thereof to a patient having, suffering from, or diagnosed with FRDA, LHON, DAD, Leigh's disease, NARP, MNGIE, MERRF, and/or MELAS.

In another embodiment, the compositions and methods described herein include co-administering a therapeutically effective amount of one or more tetracyclic pyrazinoindoles and/or pharmaceutically acceptable salts thereof and one or more of Coenzyme Q10 and analogs and derivatives thereof, such as idebenone, ubiquinone, ubidecarenone, and the like, and/or pharmaceutically acceptable salts thereof to a patient having, suffering from, or diagnosed with FRDA, LHON, DAD, Leigh's disease, NARP, MNGIE, MERRF, and/or MELAS.

In another embodiment, the compositions and methods described herein include co-administering a therapeutically effective amount of one or more tetracyclic pyrazinoindoles and/or pharmaceutically acceptable salts thereof and one or more dimebolins, such as dimebon, and the like, and/or pharmaceutically acceptable salts thereof to a patient having, suffering from, or diagnosed with FRDA, LHON, DAD, Leigh's disease, NARP, MNGIE, MERRF, and/or MELAS.

In another embodiment, the compositions and methods described herein include co-administering a therapeutically effective amount of one or more tetracyclic pyrazinoindoles and/or pharmaceutically acceptable salts thereof and one or more of vitamin C, vitamin E, thiamine, and/or riboflavin, and/or pharmaceutically acceptable salts thereof to a patient having, suffering from, or diagnosed with FRDA, LHON, DAD, Leigh's disease, NARP, MNGIE, MERRF, and/or MELAS.

In another embodiment, the compositions and methods described herein include co-administering a therapeutically effective amount of one or more tetracyclic pyrazinoindoles and/or pharmaceutically acceptable salts thereof and trolox, or a pharmaceutically acceptable salt thereof to a patient having, suffering from, or diagnosed with FRDA, LHON, DAD, Leigh's disease, NARP, MNGIE, MERRF, and/or MELAS.

In another embodiment, the compositions and methods described herein include co-administering a therapeutically effective amount of one or more tetracyclic pyrazinoindoles and/or pharmaceutically acceptable salts thereof and alpha lipoic acid, or a pharmaceutically acceptable salt thereof to a patient having, suffering from, or diagnosed with FRDA, LHON, DAD, Leigh's disease, NARP, MNGIE, MERRF, and/or MELAS.

In another embodiment, the compositions and methods described herein include co-administering a therapeutically effective amount of one or more tetracyclic pyrazinoindoles and/or pharmaceutically acceptable salts thereof and pyruvate, or a pharmaceutically acceptable salt thereof to a patient having, suffering from, or diagnosed with FRDA, LHON, DAD, Leigh's disease, NARP, MNGIE, MERRF, and/or MELAS.

In another embodiment, the compositions and methods described herein include co-administering a therapeutically effective amount of one or more tetracyclic pyrazinoindoles and/or pharmaceutically acceptable salts thereof and creatine, or a pharmaceutically acceptable salt thereof to a patient having, suffering from, or diagnosed with FRDA, LHON, DAD, Leigh's disease, NARP, MNGIE, MERRF, and/or MELAS.

In another embodiment, the compositions and methods described herein include co-administering a therapeutically effective amount of one or more tetracyclic pyrazinoindoles and/or pharmaceutically acceptable salts thereof and dichloroacetate, or a pharmaceutically acceptable salt thereof to a patient having, suffering from, or diagnosed with FRDA, LHON, DAD, Leigh's disease, NARP, MNGIE, MERRF, and/or MELAS.

In another embodiment, the compositions and methods described herein include co-administering a therapeutically effective amount of one or more tetracyclic pyrazinoindoles and/or pharmaceutically acceptable salts thereof and one or more of carnitine, and analogs and derivatives thereof, such as acetylcarnitine, and the like, and/or pharmaceutically acceptable salts thereof to a patient having, suffering from, or diagnosed with FRDA, LHON, DAD, Leigh's disease, NARP, MNGIE, MERRF, and/or MELAS.

In another embodiment, the compositions and methods described herein include co-administering a therapeutically effective amount of one or more tetracyclic pyrazinoindoles and/or pharmaceutically acceptable salts thereof and curcumin, or a pharmaceutically acceptable salt thereof to a patient having, suffering from, or diagnosed with FRDA, LHON, DAD, Leigh's disease, NARP, MNGIE, MERRF, and/or MELAS.

In another embodiment, the compositions and methods described herein include co-administering a therapeutically effective amount of one or more tetracyclic pyrazinoindoles and/or pharmaceutically acceptable salts thereof and acetyluridine, or a pharmaceutically acceptable salt thereof to a patient having, suffering from, or diagnosed with FRDA, LHON, DAD, Leigh's disease, NARP, MNGIE, MERRF, and/or MELAS.

It is to be understood that in each of the foregoing methods, all combinations of compounds described herein may be co-administered, such as but not limited to administering a therapeutically effective amount of one or more tetracyclic pyrazinoindoles and/or pharmaceutically acceptable salts thereof, and administering a therapeutically effective amount of idebenone and/or pharmaceutically acceptable salts thereof, and administering a therapeutically effective amount of Trolox to a patient.

In another embodiment, pharmaceutical compositions are described herein. Illustrative pharmaceutical compositions include dosage forms of one or more tetracyclic pyrazinoindoles and/or pharmaceutically acceptable salts thereof, and one or more pharmaceutically acceptable carriers, excipients, and/or diluents therefor. Other illustrative pharmaceutical compositions include dosage forms of mixtures of one or more tetracyclic pyrazinoindoles and/or pharmaceutically acceptable salts thereof, and one or more other pharmaceutically effective agents, and one or more pharmaceutically acceptable carriers, excipients, and/or diluents therefore, such as (a) mixtures of one or more tetracyclic pyrazinoindoles and/or pharmaceutically acceptable salts thereof, and one or more dimebolins and/or pharmaceutically acceptable salts thereof, (b) mixtures of one or more tetracyclic pyrazinoindoles and/or pharmaceutically acceptable salts thereof, and idebenone and/or pharmaceutically acceptable salts thereof, (c) mixtures of one or more tetracyclic pyrazinoindoles and/or pharmaceutically acceptable salts thereof, and trolox and/or pharmaceutically acceptable salts thereof, (d) mixtures of one or more tetracyclic pyrazinoindoles and/or pharmaceutically acceptable salts thereof, and coenzyme Q10, and analogs and derivatives thereof, such as idebenone, ubiquinone, ubidecarenone, coenzyme Q, and the like, (e) mixtures of one or more tetracyclic pyrazinoindoles and/or pharmaceutically acceptable salts thereof, and Vitamin E and/or pharmaceutically acceptable salts thereof, (f) mixtures of one or more tetracyclic pyrazinoindoles and/or pharmaceutically acceptable salts thereof, and certain vitamins, such as vitamin C, vitamin E, thiamine, and/or riboflavin, and/or pharmaceutically acceptable salts thereof, (g) mixtures of one or more tetracyclic pyrazinoindoles and/or pharmaceutically acceptable salts thereof, and carnitine and/or pharmaceutically acceptable salts thereof, (h) mixtures of one or more tetracyclic pyrazinoindoles and/or pharmaceutically acceptable salts thereof, and acetylcarnitine and/or pharmaceutically acceptable salts thereof, (i) mixtures of one or more tetracyclic pyrazinoindoles and/or pharmaceutically acceptable salts thereof, and acetyluridine and/or pharmaceutically acceptable salts thereof, (j) mixtures of one or more tetracyclic pyrazinoindoles and/or pharmaceutically acceptable salts thereof, and curcumin and/or pharmaceutically acceptable salts thereof, (k) mixtures of one or more tetracyclic pyrazinoindoles and/or pharmaceutically acceptable salts thereof, and dichloroacetate and/or pharmaceutically acceptable salts thereof, (l) mixtures of one or more tetracyclic pyrazinoindoles and/or pharmaceutically acceptable salts thereof, and pyruvate and/or pharmaceutically acceptable salts thereof, (m) mixtures of one or more tetracyclic pyrazinoindoles and/or pharmaceutically acceptable salts thereof, and thiamine and/or pharmaceutically acceptable salts thereof, (n) mixtures of one or more tetracyclic pyrazinoindoles and/or pharmaceutically acceptable salts thereof, and riboflavin, (o) mixtures of one or more tetracyclic pyrazinoindoles and/or pharmaceutically acceptable salts thereof, and creatine and/or pharmaceutically acceptable salts thereof, (p) mixtures of one or more tetracyclic pyrazinoindoles and/or pharmaceutically acceptable salts thereof, idebenone and/or pharmaceutically acceptable salts thereof, and trolox and/or pharmaceutically acceptable salts thereof. Other illustrative formulations include "sandwich" formulations where two or more separate drug dosage forms are conveniently adhered one to the other for simultaneous co-administration.

As used herein, the term "tetracyclic pyrazinoindole" generally refers to hydrogenated pyrazinoindoles that include a fused ring, such as a cyclohexane ring or piperidine ring, each of which may be saturated or unsaturated, and pharmaceutically acceptable salts of any of the foregoing. Accordingly, is to be understood that in each of the foregoing, any corresponding pharmaceutically acceptable salt is also included in the illustrative embodiments described herein. Illustratively, the fused ring bridges the indole and the pyrazine portions of the pyrazinoindole. It is also to be understood that derivatives of the illustrative tetracyclic pyrazinoindoles described herein, which are also tetracyclic pyrazinoindoles, are included in the term. Illustrative derivatives include, but are not limited to, both those compounds that may be synthetically prepared from the compounds described herein, as well as those compounds that may be prepared in a similar way as those described herein, but differing in the selection of starting materials. In addition, described herein are other illustrative tetracyclic pyrazinoindoles of formulae (I), (Ia), (Ib), (Ic), (II), (III), and (IV). The formulae include various functional groups on aromatic rings, such as $R^a$. It is to be understood that derivatives of those compounds also include the compounds having for example different functional groups on those aromatic rings than those explicitly set forth in the definition of formulae (I), (Ia), (Ib), (Ic), (II), (III), and (IV). In addition, it is to be understood that derivatives of those compounds also include the compounds having those same or different functional groups at different positions on the aromatic ring. Similarly, derivatives include parallel variations of other functional groups on the compounds described herein, such as $R^N$, and the like. In addition, as used herein the term tetracyclic pyrazinoindole also refers to the corresponding prodrug derivatives of the compounds described herein, and including prodrugs of the various analogs and derivatives thereof.

It is also to be understood that analogs of the illustrative tetracyclic pyrazinoindoles described herein, which are structurally similar, or are similar based on biochemical and/or biological activity, whether or not they are also tetracyclic pyrazinoindoles, are also included in the term. Illustrative analogs include, but are not limited to, the corresponding ring expanded or ring contracted core structures of the compounds described herein, such as but not limited to the corresponding cycloheptane, cyclopentane, homopiperidine, pyrrolidine, and like ring systems. Other illustrative analogs include, but are not limited to, the corresponding ring systems that include additional heteroatoms, such as the corresponding pyrimidine, azaindole, pyridazine, and like ring systems. Therefore, it is to be understood that all such analogs compounds are also considered to be tetracyclic pyrazinoindoles.

In one embodiment the tetracyclic pyrazinoindole is a compound of formula (I)

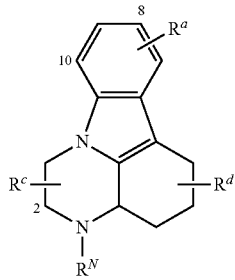

(I)

or a pharmaceutically acceptable salt thereof, wherein $R^a$ is hydrogen, or $R^a$ represents 1 to 4 substituents, each independently selected from halo and hydroxy, and alkoxy, acyloxy, alkyl, heteroalkyl, cycloalkyl, cycloheteroalkyl, aryl, heteroaryl, arylalkyl, or heteroarylalkyl, each of which is optionally substituted;

$R^c$ is hydrogen, or $R^c$ represents 1 or 2 substituents, each independently selected from alkyl, heteroalkyl, cycloalkyl, cycloheteroalkyl, aryl, heteroaryl, arylalkyl, and heteroarylalkyl, each of which is optionally substituted;

$R^d$ is hydrogen, or $R^d$ represents 1 or 2 substituents, each independently selected from alkyl, heteroalkyl, cycloalkyl, cycloheteroalkyl, aryl, heteroaryl, arylalkyl, and heteroarylalkyl, each of which is optionally substituted; and $R^N$ is hydrogen or hydroxy, or alkoxy, acyloxy, alkyl, heteroalkyl, cycloalkyl, cycloheteroalkyl, aryl, heteroaryl, arylalkyl, or heteroarylalkyl, each of which is optionally substituted; or $R^N$ and the attached nitrogen form an amide, carbamate, or urea, or thiono derivative thereof; or $R^N$ and the attached nitrogen form an amine prodrug.

In another embodiment, $R^a$ is hydrogen. In another embodiment, $R^a$ represents 1 to 4 substituents, each independently selected from halo (including F, Cl, and Br), optionally substituted hydroxy (including alkoxy and acyloxy), acyl (including $C(O)NHNH_2$ and $CO_2Et$), alkyl (including methyl), heteroalkyl, cycloalkyl (including cyclohexyl, cyclododecyl, adamantyl, and the like), aryl (including 4-methoxyphenyl), and arylalkyl, each of which is optionally substituted. In another embodiment, $R^c$ is hydrogen. In another embodiment, $R^c$ represents 1 or 2 substituents, each independently selected from alkyl and aryl (including phenyl), each of which is optionally substituted. In another embodiment, $R^N$ is H or acyl. In another embodiment, $R^N$ is alkyl, heteroalkyl, aryl, or arylalkyl, each of which is optionally substituted.

In another embodiment, the tetracyclic pyrazinoindole is a compound of formula (Ia)

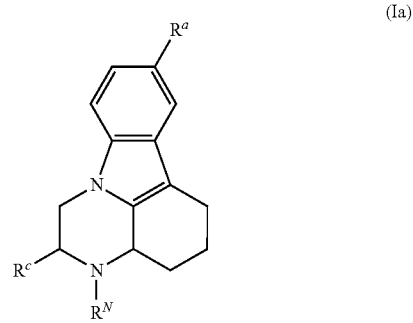

(Ia)

or a pharmaceutically acceptable salt thereof, wherein $R^a$ is hydrogen, halo, or hydroxy, or alkoxy, acyloxy, alkyl, heteroalkyl, cycloalkyl, cycloheteroalkyl, aryl, heteroaryl, arylalkyl, or heteroarylalkyl, each of which is optionally substituted;

$R^c$ is hydrogen, or alkyl, heteroalkyl, cycloalkyl, cycloheteroalkyl, aryl, heteroaryl, arylalkyl, or heteroarylalkyl, each of which is optionally substituted; and $R^N$ is hydrogen or hydroxy, or alkoxy, acyloxy, alkyl, heteroalkyl, cycloalkyl, cycloheteroalkyl, aryl, heteroaryl, arylalkyl, or heteroarylalkyl, each of which is optionally substituted; or $R^N$ and the attached nitrogen form an amide, carbamate, or urea, or thiono derivative thereof; or $R^N$ and the attached nitrogen form an amine prodrug.

In another embodiment, $R^a$ is selected from halo (including F, Cl, and Br), optionally substituted hydroxy (including methoxy, acetoxy), acyl (including $C(O)NHNH_2$ and $CO_2Et$), alkyl (including methyl), heteroalkyl, cycloalkyl (including cyclohexyl, cyclododecyl, adamantyl, and the like), aryl (including 4-methoxyphenyl), or arylalkyl, each of which is optionally substituted. In another embodiment, $R^c$ is selected from alkyl and aryl (including phenyl), each of which is optionally substituted. In another embodiment, $R^N$ is H or acyl. In another embodiment, $R^N$ is alkyl, heteroalkyl, aryl, or arylalkyl, each of which is optionally substituted.

In another embodiment, the tetracyclic pyrazinoindole is a compound of formula (Ib)

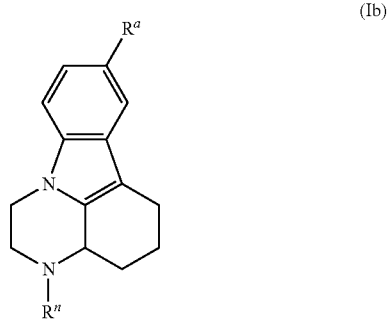

(Ib)

or a pharmaceutically acceptable salt thereof, wherein $R^a$ is hydrogen, halo, or hydroxy, or alkoxy, acyloxy, alkyl, heteroalkyl, cycloalkyl, cycloheteroalkyl, aryl, heteroaryl, arylalkyl, or heteroarylalkyl, each of which is optionally substituted; and $R^N$ is hydrogen or hydroxy, or alkoxy, acyloxy, alkyl, heteroalkyl, cycloalkyl, cycloheteroalkyl, aryl, heteroaryl, arylalkyl, or heteroarylalkyl, each of which is optionally substituted; or $R^N$ and the attached nitrogen form an amide, carbamate, or urea, or thiono derivative thereof; or $R^N$ and the attached nitrogen form an amine prodrug.

In another embodiment, $R^a$ is selected from halo (including F, Cl, and Br), optionally substituted hydroxy (including methoxy, acetoxy), acyl (including C(O)NHNH$_2$ and CO$_2$Et), alkyl (including methyl), heteroalkyl, cycloalkyl (including cyclohexyl, cyclododecyl, adamantyl, and the like), aryl (including 4-methoxyphenyl), or arylalkyl, each of which is optionally substituted. In another embodiment, $R^N$ is H or acyl. In another embodiment, $R^N$ is alkyl, heteroalkyl, aryl, or arylalkyl, each of which is optionally substituted.

In another embodiment, the tetracyclic pyrazinoindole is a compound of formula (Ic)

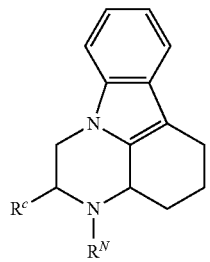

(Ic)

or a pharmaceutically acceptable salt thereof, wherein $R^c$ is hydrogen, or alkyl, heteroalkyl, cycloalkyl, cycloheteroalkyl, aryl, heteroaryl, arylalkyl, or heteroarylalkyl, each of which is optionally substituted; and $R^N$ is hydrogen or hydroxy, or alkoxy, acyloxy, alkyl, heteroalkyl, cycloalkyl, cycloheteroalkyl, aryl, heteroaryl, arylalkyl, or heteroarylalkyl, each of which is optionally substituted; or $R^N$ and the attached nitrogen form an amide, carbamate, or urea, or thiono derivative thereof; or $R^N$ and the attached nitrogen form an amine prodrug.

In another embodiment, $R^c$ is selected from alkyl and aryl (including phenyl), each of which is optionally substituted. In another embodiment, $R^N$ is H or acyl. In another embodiment, $R^N$ is alkyl, heteroalkyl, aryl, or arylalkyl, each of which is optionally substituted.

In another embodiment of any of formulae (I) to (Ic), $R^N$ is H. In another embodiment of any of formulae (I) to (Ic), $R^N$ is alkyl, such as methyl, ethyl, butyl, and the like. In another embodiment of any of formulae (I) to (Ic), $R^N$ is substituted alkyl, such as cyanomethyl, haloalkyl, hydroxyalkyl, aminoalkyl (including 2-aminoethyl, 2-diethylaminoethyl), hydroxyalkylaminoalkyl, aminoalkylhydroxyalkyl (including N-methylpiperazinyl-2-hydroxypropyl), aminoalkylaminoalkyl, aminoalkylaminoalkylhydroxyalkyl (including Et$_2$N—(CH$_2$)S—NH—CH$_2$—CH(OH)—CH$_2$, Me$_2$N—(CH$_2$)—NH—CH$_2$—CH(OH)—CH$_2$), aminocarbonylalkyl (including methylcarbonylmethyl, 2-aminocarbonylethyl, 3-methylpipidinylcarbonylmethyl), and the like.

In another embodiment of any of formulae (I) to (Ic), $R^N$ is aryl, such as 4-(3,4-dimethoxyphenyl)-2-thiazolyl, 1-methyl-3-nitro-1H-1,2,4-triazol-5-yl, and the like. In another embodiment of any of formulae (I) to (Ic), $R^N$ is acyl, such as optionally substituted alkanoyl (including 7,7,7-trifluoroheptanoyl, diethylaminoacetyl), or optionally substituted benzoyl (including 3,4,5-trimethoxybenzoyl, 2-fluorobenzoyl).

In another embodiment of any of formulae (I) to (Ic), $R^a$ is at C-8 (para to the nitrogen). In another embodiment of any of formulae (I) to (Ic), $R^a$ is at C-8 and C-10 (including 8,10-dimethyl). In another embodiment of any of formulae (I) to (Ic), $R^a$ represents 0 to 4 substituents selected from silyl (including trimethylsilyl, diphenylmethylsily, and the like), halo (including fluoro, chloro, and bromo), nitro, cyano, hydroxyl, alkyl (including methyl, ethyl, isopropyl, tertbutyl, and the like), cycloalkyl (including cyclopentyl, cycloheptyl, cyclodecanyl, adamantyl, and the like), cycloalkenyl (including cyclopentenyl, cyclohexenyl, cyclohexadienyl, and the like), hydroxyalkyl and hydroxycycloalkyl (including hydroxymethyl, phenylhydroxymethyl, hydroxycyclopentyl, dihydroxycyclohexyl, and the like), aryl (including phenyl, methoxyphenyl, and the like), alkoxy, alkoxyalkyl, cycloalkoxyl, and aryloxy (including methoxy, isobutoxy, cyclohexyloxy, benzyloxy, methoxyladamantyl, phenoxy, methoxylmethyl, methoxyphenoxy, and the like), amino (including NH$_2$, piperidinyl, quinuclidinyl, and the like), carbonyl, and carboxyl and derivatives thereof (including carboxy, acetoxy, ethoxycarbonyl, hydrazidocarbonyl, and the like), and others.

In another embodiment of any of formulae (I) to (Ic), $R^a$ is at C-7. In another embodiment of any of formulae (I) to (Ic), $R^a$ is at C-8. In another embodiment of any of formulae (I) to (Ic), $R^a$ is at C-9. In another embodiment of any of formulae (I) to (Ic), $R^a$ is at C-10. In another embodiment of any of formulae (I) to (Ic), $R^a$ is at C-7 and C-10. In another embodiment of any of formulae (I) to (Ic), $R^a$ is at C-8 and C-10. In another embodiment of any of formulae (I) to (Ic), $R^a$ is selected from 9-chloro, 7-amino-10-methyl, 10-methyl, and 8,10-dimethyl. In another embodiment of any of formulae (I) to (Ic), $R^a$ is methyl; and $R^c$ is phenyl or 4-MeO-phenyl.

In another embodiment of any of formulae (I) to (Ic), $R^a$ is one or more of the following:

| | | |
|---|---|---|
| trimethylsilyl | 1-adamantyl | cyclohexyloxy |
| fluoro | cyclopent-1-ene-yl | benzyloxy |
| chloro | cyclohex-1-ene-yl | phenoxy |
| bromo | cyclohexa-1,3-diene-yl | 4-MeO-phenoxy |
| nitro | hydroxymethyl | amino |
| hydroxy | phenyl-hydroxymethyl | (4-piperidinyl) |
| ethyl | 1-OH-1-cyclopentyl | 3-quinulidinyl |
| isopropyl | dihydroxycyclohexyl | hydrazidocarbonyl |
| tert-butyl | methoxymethyl | carboxy |
| 1-cyclopentyl | 2-MeO-2-adamantyl | acetoxy |
| cycloheptyl | methoxy | ethoxy carbonyl |
| cyclododecanyl | iso-butoxy | |

In another embodiment of any of formulae (I) to (Ic), $R^c$ is at C-2. In another embodiment of any of formulae (I) to (Ic), $R^c$ represents 0 to 2 substituents selected from alkyl (including methyl, ethyl, isopropyl, and the like) and aryl (including phenyl, methoxyphenyl, and the like). In another embodiment of any of formulae (I) to (Ic), $R^c$ is at C-2.

In another embodiment the tetracyclic pyrazinoindole is a compound of formulae (II) or (III)

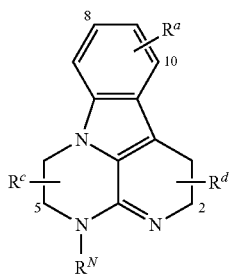

(II)

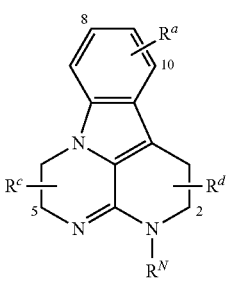

(III)

or a pharmaceutically acceptable salt thereof, wherein $R^a$ is hydrogen, or $R^a$ represents 1 to 4 substituents, each independently selected from halo and hydroxy, and alkoxy, acyloxy, alkyl, heteroalkyl, cycloalkyl, cycloheteroalkyl, aryl, heteroaryl, arylalkyl, or heteroarylalkyl, each of which is optionally substituted;

$R^c$ is hydrogen, or $R^c$ represents 1 or 2 substituents, each independently selected from alkyl, heteroalkyl, cycloalkyl, cycloheteroalkyl, aryl, heteroaryl, arylalkyl, and heteroarylalkyl, each of which is optionally substituted;

$R^d$ is hydrogen, or $R^d$ represents 1 or 2 substituents, each independently selected from alkyl, heteroalkyl, cycloalkyl, cycloheteroalkyl, aryl, heteroaryl, arylalkyl, and heteroarylalkyl, each of which is optionally substituted; and $R^N$ is hydrogen or hydroxy, or alkoxy, acyloxy, alkyl, heteroalkyl, cycloalkyl, cycloheteroalkyl, aryl, heteroaryl, arylalkyl, or heteroarylalkyl, each of which is optionally substituted; or $R^N$ and the attached nitrogen form an amide, carbamate, or urea, or thiono derivative thereof; or $R^N$ and the attached nitrogen form an amine prodrug.

In another embodiment the tetracyclic pyrazinoindole is a compound of formula (IV)

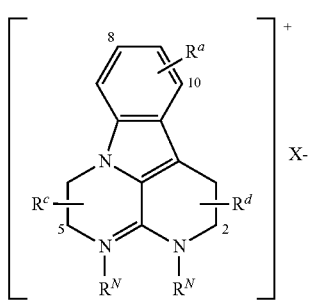

(IV)

or a pharmaceutically acceptable salt thereof, wherein $R^a$ is hydrogen, or $R^a$ represents 1 to 4 substituents, each independently selected from halo and hydroxy, and alkoxy, acyloxy, alkyl, heteroalkyl, cycloalkyl, cycloheteroalkyl, aryl, heteroaryl, arylalkyl, or heteroarylalkyl, each of which is optionally substituted;

$R^c$ is hydrogen, or $R^c$ represents 1 or 2 substituents, each independently selected from alkyl, heteroalkyl, cycloalkyl, cycloheteroalkyl, aryl, heteroaryl, arylalkyl, and heteroarylalkyl, each of which is optionally substituted;

$R^d$ is hydrogen, or $R^d$ represents 1 or 2 substituents, each independently selected from alkyl, heteroalkyl, cycloalkyl, cycloheteroalkyl, aryl, heteroaryl, arylalkyl, and heteroarylalkyl, each of which is optionally substituted; and $R^N$ is independently selected in each instance from hydrogen and hydroxy, and alkoxy, acyloxy, alkyl, heteroalkyl, cycloalkyl, cycloheteroalkyl, aryl, heteroaryl, arylalkyl, and heteroarylalkyl, each of which is optionally substituted; or one or more $R^N$ and the attached nitrogen form an amide, carbamate, or urea, or thiono derivative thereof; or one or more $R^N$ and the attached nitrogen form an amine prodrug; and X is a pharmaceutically acceptable anion, such as chloride, mesylate, and the like.

In another embodiment, compounds of formulae (II), (III), and (IV) are described wherein $R^a$ is hydrogen, halo, hydroxyl, or alkyl, alkoxy, cycloalkyl, or arylalkoxy, each of which is optionally substituted. In another embodiment, compounds of formulae (II), (III), and (IV) are described wherein $R^a$ is hydrogen, halo, hydroxyl, alkyl, alkoxy, cycloalkyl, or arylalkoxy. In another embodiment, compounds of formulae (II), (III), and (IV) are described wherein $R^a$ is at C-7. In another embodiment, compounds of formulae (II), (III), and (IV) are described wherein $R^a$ is at C-8. In another embodiment, compounds of formulae (II), (III), and (IV) are described wherein $R^a$ is at C-9.

In another embodiment, compounds of formulae (II), (III), and (IV) and each of the foregoing embodiments are described wherein $R^c$ is hydrogen. In another embodiment, compounds of formulae (II), (III), and (IV) and each of the foregoing embodiments are described wherein $R^c$ is optionally substituted alkyl. In another embodiment, compounds of formulae (II), (III), and (IV) and each of the foregoing embodiments are described wherein $R^c$ is alkyl. In another embodiment, compounds of formulae (II), (III), and (IV) and each of the foregoing embodiments are described wherein $R^c$ is at C-5.

In another embodiment, compounds of formulae (II), (III), and (IV) and each of the foregoing embodiments are described wherein $R^d$ is hydrogen.

In another embodiment, compounds of formulae (II), (III), and (IV) and each of the foregoing embodiments are described wherein $R^N$ is independently selected in each instance from hydrogen, or alkyl, cycloalkyl, or arylalkyl, each of which is optionally substituted. In another embodiment, compounds of formulae (II), (III), and (IV) and each of the foregoing embodiments are described wherein $R^N$ is independently selected in each instance from hydrogen, or alkyl, cycloalkyl, or arylalkyl, each of which is optionally substituted.

In another embodiment, compounds of formulae (I), (Ia), (Ib), (II), (III), and (IV) and each of the foregoing embodiments are described wherein $R^a$ is alkyl. In another embodiment, compounds of formulae (I), (Ia), (Ib), (II), (III), and (IV) and each of the foregoing embodiments are described wherein $R^a$ is $C_1$-$C_6$ alkyl. In another embodiment, compounds of formulae (I), (Ia), (Ib), (II), (III), and (IV) and each of the foregoing embodiments are described wherein $R^a$ is $C_1$-$C_4$ alkyl. In another embodiment, compounds of formulae (I), (Ia), (Ib), (II), (III), and (IV) and each of the foregoing embodiments are described wherein $R^a$ is $C_1$-$C_2$ alkyl. In another embodiment, compounds of formulae (I), (Ia), (Ib), (II), (III), and (IV) and each of the foregoing embodiments are described wherein $R^a$ is methyl. In another embodiment, compounds of formulae (I), (Ia), (Ib), (II), (III), and (IV) and each of the foregoing embodiments are described wherein $R^a$ is cycloalkyl. In another embodiment, compounds of formulae (I), (Ia), (Ib), (II), (III), and (IV) and each of the foregoing embodiments are described wherein $R^a$ is $C_3$-$C_8$ cycloalkyl. In another embodiment, compounds of formulae (I), (Ia), (Ib), (II), (III), and (IV) and each of the foregoing embodiments are described wherein $R^a$ is $C_5$-$C_6$ cycloalkyl. In another embodiment, compounds of formulae (I), (Ia), (Ib), (II), (III), and (IV) and each of the foregoing embodiments are described wherein $R^a$ is cyclohexyl. In another embodiment, compounds of formulae (I), (Ia), (Ib), (II), (III), and (IV) and each of the foregoing embodiments are described wherein $R^a$ is alkoxy. In another embodiment, compounds of formulae (I), (Ia), (Ib), (II), (III), and (IV) and each of the foregoing embodiments are described wherein $R^a$ is $C_1$-$C_6$ alkoxy. In another embodiment, compounds of formulae (I), (Ia), (Ib), (II), (III), and (IV) and each of the foregoing embodiments are described wherein $R^a$ is $C_1$-$C_4$ alkoxy. In another embodiment, compounds of formulae (I), (Ia), (Ib), (II), (III), and (IV) and each of the foregoing embodiments are described wherein $R^a$ is $C_1$-$C_2$ alkoxy. In another embodiment, compounds of formulae (I), (Ia), (Ib), (II), (III), and (IV) and each of the foregoing embodiments are described wherein $R^a$ is methoxy.

In another embodiment, compounds of formulae (I), (Ia), (Ic), (II), (III), and (IV) and each of the foregoing embodiments are described wherein $R^c$ is hydrogen.

In another embodiment, compounds of formulae (I), (II), (III), and (IV) and each of the foregoing embodiments are described wherein $R^d$ is hydrogen.

In another embodiment, compounds of formulae (I), (Ia), (Ib), (Ic), (II), (III), and (IV) and each of the foregoing embodiments are described wherein $R^N$ is hydrogen. In another embodiment, compounds of formulae (I), (Ia), (Ib), (Ic), (II), (III), and (IV) and each of the foregoing embodiments are described wherein $R^N$ is alkyl. In another embodiment, compounds of formulae (I), (Ia), (Ib), (Ic), (II), (III), and (IV) and each of the foregoing embodiments are described wherein $R^N$ is $C_1$-$C_6$ alkyl. In another embodiment, compounds of formulae (I), (Ia), (Ib), (Ic), (II), (III), and (IV) and each of the foregoing embodiments are described wherein $R^N$ is $C_1$-$C_4$ alkyl. In another embodiment, compounds of formulae (I), (Ia), (Ib), (Ic), (II), (III), and (IV) and each of the foregoing embodiments are described wherein $R^N$ is $C_1$-$C_2$ alkyl. In another embodiment, compounds of formulae (I), (Ia), (Ib), (Ic), (II), (III), and (IV) and each of the foregoing embodiments are described wherein $R^N$ is methyl. In another embodiment, compounds of formulae (I), (Ia), (Ib), (Ic), (II), (III), and (IV) and each of the foregoing embodiments are described wherein $R^N$ is cycloalkyl. In another embodiment, compounds of formulae (I), (Ia), (Ib), (Ic), (II), (III), and (IV) and each of the foregoing embodiments are described wherein $R^N$ is $C_3$-$C_8$ cycloalkyl. In another embodiment, compounds of formulae (I), (Ia), (Ib), (Ic), (II), (III), and (IV) and each of the foregoing embodiments are described wherein $R^N$ is $C_5$-$C_6$ cycloalkyl. In another embodiment, compounds of formulae (I), (Ia), (Ib), (Ic), (II), (III), and (IV) and each of the foregoing embodiments are described wherein $R^N$ is cyclohexyl.

In another embodiment, the tetracyclic pyrazinoindole is the corresponding dehydro compound of any of formulae (I) to (Ic), or embodiments thereof described herein. In another embodiment, a therapeutically effective amount of pirlindole (also known as Pirazidol and/or pirlindolum, or 2,3,3a,4,5, 6-hexahydro-8-methyl-1H-pyrazino[3,2,1-j,k]carbazole or 1,10-trimethylene-8-methyl-1,2,3,4-tetrahydropyrazino[1,2-a]indole) is included on the compositions described herein, or administered in the methods described herein. As used herein, pirlindole includes compounds of the formula:

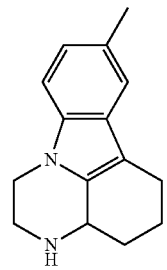 [SMILES: Cc1ccc2c(c1)c1c3n2CCNC3CCC1]

and pharmaceutically acceptable salts thereof, such as the hydrochloride salt or the mesylate salt.

In another embodiment, a therapeutically effective amount of tetrindole is administered in the methods described herein, including tetrindole (2,3,3a,4,5,6-Hexahydro-8-cyclohexyl-1H-pyrazino[3,2,1-j,k]carbazole) of the formula:

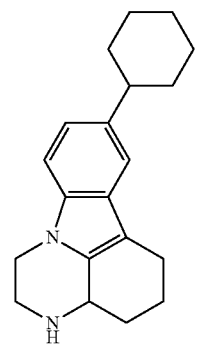 [SMILES: c1cc2c(cc1C1CCCCC1)c1c3n2CCNC3CCC1]

and pharmaceutically acceptable salts thereof, such as the mesylate salt.

In another embodiment, a therapeutically effective amount of metralindole is administered in the methods described herein, including the formula:

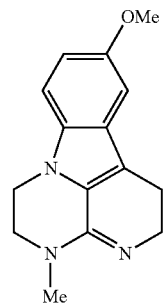 [SMILES: COc1ccc2c(c1)c1c3n2CCN(C)C3=NCC1]

and pharmaceutically acceptable salts thereof, such as the hydrochloride salt.

In each of the foregoing and following embodiments, it is to be understood that the formulae include and represent not only all pharmaceutically acceptable salts of the tetracyclic pyrazinoindoles, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non crystalline and/or amorphous forms of the compounds. The tetracyclic pyrazinoindoles described herein may be prepared according to conventional synthetic processes, including the process described by Gazengel et al., Journal of Heterocyclic Chemistry (1990), 27(7), 1947-51, the disclosure of which is incorporated herein by reference. For example, it is appreciated that the various analogs and derivatives of pirlindole itself described herein may be prepared by routine modification and optimization of the process described by Gazengel et al., such as by the appropriate selection of the corresponding starting materials used in the process.

In another embodiment, the one or more tetracyclic pyrazinoindoles are included in the compositions and methods in amounts therapeutically effective to (a) scavenge ROS, (b) stabilize mitochondria and/or (c) inhibit apoptotic cell death. Without being bound by theory, it is believed herein that the compounds, compositions, and methods described herein for treating one or more forms of FRDA, LHON, DAD, Leigh's disease, NARP, MNGIE, MERRF, MELAS, and the like may be efficacious at least in part because the one or more tetracyclic pyrazinoindoles included therein are in therapeutically effective amounts to (a) scavenge ROS, (b) stabilize mitochondria, (c) inhibit apoptotic cell death. It is appreciated herein that tetracyclic pyrazinoindoles may not function as systemic scavengers of ROS, and instead are more specific to protecting the mitochondria organelle itself. It is further appreciated herein that for certain of the diseases described, the compounds cross the blood-brain-barrier.

In another embodiment, methods are described herein for treating FRDA, LHON, DAD, Leigh's disease, NARP, MNGIE, MERRF, MELAS, and the like by administering one or more tetracyclic pyrazinoindoles, and/or pharmaceutically acceptable salts thereof, in an amount therapeutically effective to stabilize mitochondria. Without being bound by theory, it is believed herein that inhibition of apoptotic cell death by scavenging of ROS may be one of the mechanisms by which tetracyclic pyrazinoindoles are efficacious in treating FRDA, LHON, DAD, Leigh's disease, NARP, MNGIE, MERRF, MELAS, and the like.

In another embodiment, methods are described herein for treating FRDA, LHON, DAD, Leigh's disease, NARP, MNGIE, MERRF, MELAS, and the like by administering one or more tetracyclic pyrazinoindoles, and/or pharmaceutically acceptable salts thereof, in an amount therapeutically effective to inhibit apoptosis. However, without being bound by theory, it is believed herein that the therapeutic potential in FRDA, LHON, DAD, Leigh's disease, NARP, MNGIE, MERRF, MELAS, and the like of a treatment using a tetracyclic pyrazinoindole is not limited to the observed activity of compounds against apoptosis, or alternatively that other compounds capable of apoptosis intervention would be efficacious. For example, a well known chemotherapy agent vitamin E has been reported to possess lipid antioxidant activity. However, vitamin E is too lipophillic and thus permeates cell membranes poorly and cannot reach the mitochondria, the main site of ROS production (Edeas M. Pharm Res. 2011 Epub September 15. DOI 10.1007/s11095-011-0587-2).

Without being bound by theory, it is also believed herein that the success of the methods using a tetracyclic pyrazinoindole may be due at least in part to the particular pharmacokinetic characteristics and blood-brain-barrier permeability, in conjunction with the particular adverse event profile, shown by those compounds. Those abilities are contrary to what has been observed with other antioxidants, which may have an unacceptable adverse event profile, such as has been observed with etoposide, or unfavorable pharmacokinetic characteristics, such as exhibited by PNU-87663.

As used herein the term Friedreich ataxia (FA, FRDA, FRIEDREICH ATAXIA 1, OMIM# *229300) generally refers to an autosomal recessive ataxia resulting from a mutation of a gene locus on chromosome 9. As used herein, the term also includes borderline forms of Friedreich ataxia. The disease was first described in 1863 by Nikolaus Friedreich, a professor of medicine in Heidelberg, Germany. The major pathophysiologic finding in Friedreich ataxia is reportedly a dying back of axons. The degradaion is accompanied by a fibrous gliosis that does not replace the bulk of the lost fibers. Overall, the spinal cord becomes thin and the anteroposterior (AP) and transverse diameters of the thoracic cord are reduced. The dorsal spinal ganglia show shrinkage and eventual disappearance of neurons associated with proliferation of capsular cells. The posterior column degeneration accounts for the loss of position and vibration senses and the sensory ataxia. The loss of large neurons in the sensory ganglia causes extinction of tendon reflexes.

Large neurons of the dorsal root ganglia, especially lumbosacral, and nerve cells in the Clarke column are reduced in number. The posterior roots become thin. The dentate nuclei exhibit mild to moderate neuronal loss and the middle and superior cerebellar peduncles are reduced in size. Patchy loss of Purkinje cells in the superior vermis of the cerebellum and of neurons in corresponding portions of the inferior olivary nuclei is typical. Mild degenerative changes occur in the pontine and medullary nuclei and optic tracts. The cerebellar ataxia is explained by loss of the lateral and ventral spinocerebellar tracts and involvement of the Clarke column, dentate nucleus, superior vermis, and dentatorubral pathways.

The corticospinal tracts are relatively spared down to the level of the cervicomedullary junction. Beyond this point, the corticospinal tracts are severely degenerated, which becomes progressively more severe moving down the spinal cord, which explains the common finding of bilateral extensor plantar responses and weakness late in the disease. Loss of cells in the nuclei of cranial nerves VII, X, and XII results in facial weakness and speech and swallowing difficulties.

Myocardial muscle fibers also show degeneration and are replaced by macrophages and fibroblasts, where mitochondrial cell death precedes fibrosis. Chronic interstitial myocarditis occurs with hypertrophy of cardiac muscle fibers; fibers become hypertrophied and lose their striations. This is followed by swelling and vacuolation and finally interstitial fibrosis. The nuclei appear hyperchromatic and occasionally vacuolated. The cytoplasm appears granular with frequent lipofuscin depositions. Kyphoscoliosis is likely; it is secondary to spinal muscular imbalance. Accordingly, because the brain and the muscles, and especially the heart, are energy demanding organs, mitochondrial dysfunction may have a disproportionately greater negative impact on those organs.

The other mitochondrial diseases treatable using the compositions and methods described herein are similar. Brain and muscle are also usually affected in these disorders, although other tissues that have high energy requirements may also be affected. Patients can present with a wide range of clinical features in various combinations, including muscle degeneration and cardiovascular disease, movement disorders, diabetes mellitus, renal failure, dementias, and various ophthalmological symptoms. Mitochondrial disease include but are not limited to the following syndromes:

Diabetes mellitus and deafness (DAD)
Leber's hereditary optic neuropathy (LHON):
Leigh's disease, subacute sclerosing encephalopathy:
Neuropathy, ataxia, retinitis pigmentosa, and ptosis (NARP)
Myoneurogenic gastrointestinal encephalopathy (MNGIE)
Myoclonic Epilepsy with Ragged Red Fibers (MERRF)
Mitochondrial myopathy, encephalomyopathy, lactic acidosis, stroke-like symptoms (MELAS).

The first descriptions of pathogenic mitochondrial DNA (mtDNA) mutations were made 15 years ago in the late 1980s. A point mutation was discovered in the ND4 gene of complex I in a family with Leber hereditary optic neuropathy (LHON) (McKenzie M. Neurochem Res. 2004 March; 29(3):589-600, Wallace D C. Science 1988; 242:1427-1430), and large-scale deletions were detected in patients with mitochondrial myopathy (Holt I J. Nature 1988; 331: 717-719), progressive external ophthalmoplegia (Moraes C T. N. Engl. J. Med. 1989; 320:1293-1299), and Kearns-Sayre syndrome (KSS) (Zeviani M. Neurology 1988; 38: 1339-1346). The catalogue of mtDNA point mutations has now grown to well over 100 (Servidei S. Neuromuscul. Disord. 2000; 10:X-XV.), with a wide variety of clinical syndromes documented.

The deleterious effect of mtDNA mutations on energy metabolism appears to be a central pathogenic factor, and studies measuring mitochondrial respiration and electron transport chain (ETC) enzyme activities have been widely performed in many different mitochondrial diseases. Other important cellular functions performed by the mitochondria may also play a role in disease pathogenesis. Two aspects of mitochondrial function that may be involved include the generation of reactive oxygen species (ROS) and the regulation of programmed cell death, or apoptosis.

Mitochondria not only produce the majority of the cell's ATP, but are also a major source of reactive oxygen species (ROS). ROS are generated as by-products of normal oxidative metabolism and may play roles in both the activation of apoptotic pathways and the pathogenesis of disease. ROS include the highly energetic superoxide anion $(O_2.)^-$ and hydroxyl free radical (OH.) and the strong nonradical oxidant hydrogen peroxide ($H_2O_2$). In efficiently respiring mitochondria around 1-4% of oxygen consumed is directly converted into ROS (Chance, Physiol. Rev. 1979; 59:527-605, Richter, 1988; FEBS Lett. 241:1-5), with an unknown complex I site and the ubiquinone of complex III being the two major sites of ROS generation (Boveris A. In: Tissue hypoxia and ischemia eds. Reivich M. et al. 1979; 67-82. Plenum Press, New York). More recently the flavin mononucleotide group (FMN) of complex I has been proposed as the main physiologically relevant site of ROS production (Liu Y J. Neurochem. 2002; 80:780-787). Ubisemiquinone generated in the OXPHOS pathway can donate an electron to molecular oxygen ($O_2$), thus providing a constant source of $(O_2.)^-$ (Fridovich I. Annu. Rev. Biochem. 1995; 64:97-112.). $(O_2.)^-$ can attack the iron-sulfur centers in enzymes such as aconitase and complex I and II of the respiratory chain, releasing the iron and destroying catalytic function (Flint D H. 1993; J. Biol. Chem. 268:22369-22376). $(O_2.)^-$ is therefore quickly eliminated by conversion to $H_2O_2$ by the superoxide dismutases, of which there are three in mammalian systems: a cytosolic CuZn superoxide dismutase (SOD1), an intramitochondrial Mn superoxide dismutase (SOD2), and an extracellular CuZn superoxide dismutase (SOD3) (Fridovich I. Annu. Rev. Biochem. 1995; 64:97-112). $H_2O_2$ is subsequently converted to water by glutathione peroxidase (Gpx1) or catalase. In the presence of transition metals (such as iron or copper) the toxic (OH.) can be produced from $(O_2.)^-$ or $H_2O_2$ by the Haber-Weiss or Fenton reactions (Raha S et al. Trends Biochem. Sci. 2000; 25:502-508.).

ROS generation is greatest during state IV respiration when the ETC chain is reduced. At this time $O_2$ concentration increases with a concomitant increase in one-electron donors (Boveris A. 1972; Biochem. J. 128:617-630). This observation is supported by the inhibition of the ETC in vitro with various agents.

Stimulation of the intrinsic mitochondrial apoptotic pathway by ROS and mitochondrial DNA damage promotes outer membrane permeabilization and mitochondria-to-cytosol translocation of cytochrome c, AIF, or Smac/Diablo that trigger caspase-dependent or caspase-independent cytosolic signaling events (Circu M L et al. Free Radic Biol Med. 2010 Mar. 15; 48(6):749-62, Ryter S. Antioxid Redox Signal 2007; 9:49-89). In caspase-dependent signaling, cytochrome c forms the apoptosome complex with apoptotic protease-activating factor-1 (Apaf-1) and recruited pro-caspase-9 that induces cleavage of downstream effector caspases-3 and -7. Additionally, Smac/Diablo antagonizes the inhibitory effects of IAPs which enhances caspase activation. AIF mediates caspase-independent signaling through cytosol-to-nuclear translocation and induction of nuclear chromatin condensation and DNA fragmentation (Susin S A. Molecular characterization of mitochondrial apoptosis-inducing factor. Nature 1999; 397:441-446).

Central to mitochondrial permeabilization and mitochondrial release of apoptogenic factors is the permeability transition pore (PTP), a megapore spanning the inner and outer mitochondrial membrane. Of the three PTP component proteins, cyclophylin D (cypD), voltage-dependent anion channel (VDAC), and the adenine nucleotide translocase (ANT), only cypD is a permanent constituent and modulator of PTP (Baines C P. Nat Cell Biol 2007; 9:550-555, Kokoszka J E. Nature 2004; 427:461-465, Schinzel A C. Proc Natl Acad Sci USA 2005; 102:12005-12010). Key members of the anti-apoptotic (Bcl-2, Bcl-XL, and Bcl-w) and pro-apoptotic (Bax, Bak, Bad, Bim, and Bid) BcL-2 superfamily of proteins are major players in mitochondrial outer membrane permeabilization and apoptotic susceptibility (Kelekar A. Cell Biol 1998; 8:324-330). In the presence of an apoptotic stimulus, tBid promotes Bax/Bak oligomerization and membrane insertion that results in megapore formation, a highly orchestrated and active process (Eskes R. Mol Cell Biol 2000; 20:929-935, Desagher S. J Cell Biol 1999; 144:891-901). Additionally, tBid/Bax-induced mitochondrial permeabilization was shown to be mediated through interaction with TOM, a functional outer membrane translocase, the TOM complex (Ott M. J Biol Chem 2007; 282:27633-27639). The pivotal contribution of tBid to apoptotic signaling in both the mitochondrial and death receptor pathways is consistent with cross-talk between intrinsic and extrinsic apoptotic signaling. However, the intracellular regulatory events and/or mechanisms that would preferentially trigger the engagement of the mitochondrial cascade following exposure to extrinsic Fas or TNFα signals remain to be determined.

In addition, the extrinsic pathway of apoptosis is mediated by death receptors in which ligand-receptor binding initiates protein-protein interactions at cell membranes that activate initiator caspases. Major known receptors include Fas (also called CD95 or APO-1), TNF receptor 1 (TNFR1) and TNF-related apoptosis-inducing ligand (TRAIL) receptor 1 (TRAIL-R1; also called DR4) and TRAIL receptor 2 (TRAIL-R2; also called DR5) (Circu M L et al. Free Radic Biol Med. 2010 Mar. 15; 48(6):749-62, Ashkenazi A et al. Curr Opin Cell Biol 1999; 11:255-260). TRAIL-R3, TRAIL-R4 and soluble receptor, osteoprotegerin lack functional cytosolic domains and are decoy receptors where ligand binding does not transmit an apoptotic signal (LeBlanc H N et al. Cell Death Differ 2003; 10:66-75.). The death receptor is comprised of three functional extracellular ligand-binding, transmembrane, and intracellular domains. Ligands that activate death receptors belong to the TNF superfamily of cytokines; these include TNFα, Fas ligand (FasL), and TRAIL. Ligand binding induces receptor trimerization and cross-linking via disulfide bond formation, a step that is necessary for receptor stabilization and activity (Berg D et al. Cell Death Differ 2007; 14:2021-2034). Typically, apoptotic signaling is initiated by the association of death domain-containing adaptor proteins within the death domain located at the C-terminal domain of the receptor. Newer evidence suggests possible direct roles for ROS in mediating death receptor activation and apoptotic induction through ROS-induced receptor clustering and formation of lipid raft-derived signaling platforms.

In another embodiment, tetracyclic pyrazinoindoles described herein are administered at therapeutically effective doses in the range from about 1 mg/kg to about 10 mg/kg, from about 2 mg/kg to about 9 mg/kg, from about 3 mg/kg to about 8 mg/kg, from about 4 mg/kg to about 7 mg/kg, from about 4 mg/kg to about 6 mg/kg, from about 5 mg/kg to about 6 mg/kg; or from about 4 mg/kg to about 5 mg/kg.

Illustratively, tetracyclic pyrazinoindoles described herein are administered to an adult, such as an adult of average weight of about 70 kg, in the range from about 50 mg to about 500 mg, from about 75 mg to about 450 mg, from about 100 mg to about 400 mg; from about 125 mg to about 375 mg, from about 150 mg to about 375 mg, from about 175 mg to about 375 mg, from about 200 mg to about 375 mg, or from about 225 mg to about 375 mg.

Each of the foregoing may be illustratively administered q.d., b.i.d., t.i.d, or by other conventional dosing protocols, including intermittent dosing protocols that have an off period. In addition, it is to be understood that at each dosing interval, the amount of the dose may be single or divided into various unit dosage forms. In another illustrative embodiment, the daily dose is administered t.i.d.

In another embodiment, tetracyclic pyrazinoindoles described herein are administered b.i.d. or t.i.d.

In another embodiment the methods described herein include a titration step where the tetracyclic pyrazinoindole dose is gradually increased over a predetermined time period, such as a two step protocol for adults as follows: ¼ the ultimate desired dose thrice daily for 7 days, then ½ the ultimate desired dose thrice daily; or ¾ the ultimate desired dose thrice daily for 7 days, then the ultimate desired dose thrice daily; and the like. In another embodiment the methods described herein include a titration step where the dose is gradually increased over a predetermined time period, such as a three step protocol for adults as follows: ½ the ultimate desired dose thrice daily for 7 days, then ⅝ the ultimate desired dose thrice daily; or ¾ the ultimate desired dose thrice daily for 7 days, then the ultimate desired dose thrice daily; and the like. It is appreciated that the foregoing titrating dosing protocols may be administered to adults, teens, preteens, toddlers, and/or infants, and that the corresponding doses administered to preteens, toddlers, or infants, are lower, such as illustratively by a factor of about 2, about 5, or about 10, respectively, and may accordingly be based on the weight of the patient as indicated.

Optimal dosages and dosage regimens to be administered may be readily determined by routine experimentation, and it is understood that such optimal dosages and dosage regimens will vary with the mode of administration, the strength of the preparation and the advancement of the disease condition. In addition, factors associated with the particular patient being treated, including patient's sex, age, weight, diet, physical activity, time of administration and concomitant diseases, will result in the need to adjust dosages and/or regimens.

Without limiting the foregoing, it is appreciated that such lower doses of tetracyclic pyrazinoindoles may be more applicable to an ongoing, or chronic therapy, designed for continuous administration, rather than intermittent or acute administration. Accordingly, the daily dose may be divided and administered b.i.d. and/or t.i.d, although it is to be understood that q.d. dosing is described herein. It is to be understood that the illustrative doses described herein represent daily doses, and may be therefore administered q.d., b.i.d., t.i.d., and according to additional dosing protocols. In addition, it is to be understood that the doses may be single or divided.

In another embodiment of the compositions, kits, packages, and methods and uses described herein, one or more dimebolins are included with the one or more tetracyclic pyrazinoindoles.

As used herein, the term "dimebolin" generally refers to hydrogenated pyrido[4,3-b]indoles, such as the compounds described herein, and pharmaceutically acceptable salts of the foregoing. It is also to be understood that in each of the foregoing, any corresponding pharmaceutically acceptable salt is also included in the illustrative embodiments described herein. One such dimebolin is Dimebon, a known antihistamine drug that has been used clinically for many years, and has recently shown potential in the treatment of Alzheimer's disease (see, e.g., Doody et al., Lancet 2008; 372: 207-215; Bachurin et al., Annals of the New York Academy of Sciences. 2001; 939: 425-435). Each of the foregoing publications, and each additional publication cited herein, is incorporated herein in its entirety by reference. Additional dimebolins are described in PCT international application Serial No. PCT/US2009/060557.

In addition, described herein are other illustrative dimebolins of formulae (A), (B), (C), (D), and (E). The formulae include various functional groups on aromatic rings, such as $R^3$. It is to be understood that derivatives of those compounds also include the compounds having for example different functional groups on those aromatic rings than those explicitly set forth in the definition of formulae (A), (B), (C), (D), and (E). In addition, it is to be understood that derivatives of those compounds also include the compounds having those same or different functional groups at different positions on the aromatic ring. Similarly, derivatives include parallel variations of other functional groups on the compounds described herein, such as $R^1$, and the like. Illustrative derivatives include, but are not limited to, both those compounds that may be synthetically prepared from the compounds described herein, as well as those compounds that may be prepared in a similar way as those described herein, but differing in the selection of starting materials. In addition, as used herein the term dimebolins also refers to analogs of the compounds described herein. For example, illustrative analogs include, but are not limited to, those compounds that share functional and in some cases structural similarity to those compounds described herein. For example, described herein are illustrative dimebolins of formulae (A), (B), and (C) that include a 2,3,4,5-tetrahydro-1H-pyridoindole ring system. Illustrative analogs include, but are not limited to, the corresponding ring expanded compounds, such as the corresponding azepinoindole ring system, and the like. Other illustrative analogs include, but are not limited to, the corresponding ring systems that include additional heteroatoms, such as the corresponding pyridazinoindole ring system, and the like. Therefore, it is to be understood that all such compounds are also considered to be dimebolins, In addition, as used herein the term dimebolins also refers to prodrug derivatives of the compounds described herein, and including prodrugs of the various analogs and derivatives thereof.

In another embodiment, dimebolins of formula (A)

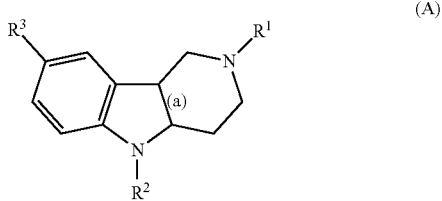

(A)

or a pharmaceutically acceptable salt thereof are described, wherein $R^1$ is hydrogen, or alkyl, heteroalkyl, cycloalkyl, cycloheteroalkyl, aryl, heteroaryl, arylalkyl, or heteroarylalkyl, each of which is optionally substituted; or $R^1$ and the attached nitrogen form an amide, carbamate, or urea, or a thiono derivative thereof; or $R^1$ and the attached nitrogen form an amine prodrug or arylalkyl; $R^2$ is hydrogen, or alkyl or arylalkyl, each of which is optionally substituted; $R^3$ is hydrogen, halo, or hydroxy, or alkoxy, acyloxy, alkyl, heteroalkyl, cycloalkyl, cycloheteroalkyl, aryl, heteroaryl, arylalkyl, or heteroarylalkyl, each of which is optionally substituted; and bond (a) is a single bond or a double bond. In another embodiment, dimebolins of formula (A) are described wherein $R^1$ is alkyl or arylalkyl; $R^2$ is hydrogen, benzyl, or 6-methylpyridinyl-3-ethyl; $R^3$ is hydrogen, alkyl, or halo; and bond (a) is a single bond or a double bond.

In another embodiment, dimebolins of formula (A) wherein $R^1$ is methyl, ethyl or benzyl are described. In another embodiment, dimebolins of formula (A) wherein $R^2$ is hydrogen, benzyl, or 6-methylpyridinyl-3-ethyl are described. In another embodiment, dimebolins of formula (A) wherein $R^3$ is hydrogen, methyl, or bromo are described. In another embodiment, dimebolins of formula (A) wherein bond (a) is a single bond; $R^1$ and $R^3$ are each methyl; and $R^2$ is hydrogen are described. In another embodiment, dimebolins of formula (A) wherein bond (a) is a single bond; and the ring fusion is cis are described. In another embodiment, dimebolin of formula (A) wherein bond (a) is a double bond; $R^1$ is ethyl or benzyl; and $R^2$ and $R^3$ are each hydrogen; or $R^1$ and $R^3$ are each methyl; and $R^2$ is benzyl; or $R^1$ is methyl; $R^2$ is 6-methylpyridinyl-3-ethyl; and $R^3$ is hydrogen; or $R^1$ and $R^3$ are each methyl; and $R^2$ is 6-methylpyridinyl-3-ethyl; or $R^1$ is methyl; $R^2$ is hydrogen; and $R^3$ is hydrogen or methyl; or $R^1$ is methyl; $R^2$ is hydrogen; and $R^3$ is bromo are described. In another embodiment, dimebolin of formula (A) where $R^1$ is selected from the group consisting of alkyl, lower alkyl and arylalkyl, $R^2$ is selected from the group consisting of hydrogen, arylalkyl and substituted heteroarylalkyl; and $R^3$ is selected from the group consisting of hydrogen, alkyl, lower alkyl and halo are described.

In one variation, $R^1$ is alkyl, such as an alkyl selected from the group consisting of $C_i$-$C_{i5}$alkyl, $C_{10}$-$C_{15}$alkyl, $C_i$-$C_{iO}$alkyl, $C_2$-$C_{15}$alkyl, $C_2$-$C_{10}$alkyl, $C_2$-$C_8$alkyl, $C_4$-$C_8$alkyl, $C_6$-$C_8$alkyl, $C_6$-$C_{15}$alkyl, $C_{15}$-$C_{20}$alkyl; $C_i$-$C_8$alkyl and $C_i$-$C\beta$alkyl. In another variation, $R^1$ is arylalkyl. In another variation, $R^1$ is lower alkyl, such as a lower alkyl selected from the group consisting of $C_i$-$C_2$-alkyl, $C_i$-$C_4$alkyl, $C_2$-$C_4$alkyl, $C_i$-$C_5$alkyl, $C_i$-$C_3$alkyl, and $C_2$-$C_5$alkyl. In another variation, $R^1$ is a straight chain alkyl group. In another variation, $R^1$ is a branched alkyl group. In another variation, $R^1$ is a cyclic alkyl group. In another variation, $R^1$ is methyl. In another variation, $R^1$ is ethyl. In another variation, $R^1$ is methyl or ethyl. In another variation, $R^1$ is methyl or an arylalkyl group such as benzyl. In another variation, $R^1$ is ethyl or an arylalkyl group such as benzyl. In another variation, $R^1$ is an arylalkyl group. In another variation, $R^1$ is an arylalkyl group where any one of the alkyl or lower alkyl substituents listed in the preceding paragraphs is further substituted with an aryl group (e.g., Ar—$C_1$-$C_6$ alkyl, Ar—$C_1$-$C_3$ alkyl OrAr-$C_1$-$C_{1S}$ alkyl). In another variation, $R^1$ is an arylalkyl group where any one of the alkyl or lower alkyl substituents listed in the preceding paragraphs is substituted with a single ring aryl residue. In another variation, $R^1$ is an arylalkyl group where any one of the alkyl or lower alkyl substituents listed in the preceding paragraphs is further substituted with a phenyl group (e.g., Ph-$C_i$-$C_6$alkyl or Ph-$CrC_3$alkyl, Ph-$C_i$-$C_{15}$alkyl). In another variation, $R^1$ is benzyl. All of the variations for $R^1$ are to be understood to be described and to be combined with any of the variations stated below for $R^2$ and $R^3$ the same as if each and every combination of $R^1$, $R^2$ and $R^3$ were specifically and individually listed.

In another variation, $R^2$ is H. In another variation, $R^2$ is an arylalkyl group. In another variation, $R^2$ is a substituted heteroarylalkyl group. In another variation, $R^2$ is hydrogen or an arylalkyl group. In another variation, $R^2$ is hydrogen or a substituted heteroarylalkyl group. In another variation, $R^2$ is an arylalkyl group or a substituted heteroarylalkyl group. In another variation, $R^2$ is selected from the group consisting of hydrogen, an arylalkyl group and a substituted heteroarylalkyl group. In another variation, $R^2$ is an arylalkyl group where $R^2$ can be any one of the arylalkyl groups noted for $R^1$ above, the same as if each and every arylalkyl variation listed for $R^1$ is separately and individually listed for $R^2$. In another variation, $R^2$ is a substituted heteroarylalkyl group, where the alkyl moiety of the heteroarylalkyl can be any alkyl or lower alkyl group, such as those listed above for $R^1$. In another variation, $R^2$ is a substituted heteroarylalkyl where the heteroaryl group is substituted with 1 to 3 $C_1$-$C_3$ alkyl substituents (e.g., 6-methyl-3-pyridylethyl). In another variation, R is a substituted heteroarylalkyl group wherein the heteroaryl group is substituted with 1 to 3 methyl groups. In another variation, $R^2$ is a substituted heteroarylalkyl group wherein the heteroaryl group is substituted with one lower alkyl substituent. In another variation, $R^2$ is a substituted heteroarylalkyl group wherein the heteroaryl group is substituted with one $C_1$-$C_3$ alkyl substituent. In one variation, $R^2$ is a substituted heteroarylalkyl group wherein the heteroaryl group is substituted with one or two methyl groups. In another variation, $R^2$ is a substituted heteroarylalkyl group wherein the heteroaryl group is substituted with one methyl group.

In other variations, $R^2$ is any one of the substituted heteroarylalkyl groups in the immediately preceding paragraph where the heteroaryl moiety of the heteroarylalkyl group is a single ring heteroaryl group. In other variations, $R^2$ is any one of the substituted heteroarylalkyl groups in the immediately preceding paragraph where the heteroaryl moiety of the heteroarylalkyl group is a multiple condensed ring heteroaryl group. In other variations, $R^2$ is any one of the substituted heteroarylalkyl groups in the immediately preceding paragraph where the heteroarylalkyl moiety is a pyridyl group (Py). In one variation, $R^2$ is 6-$CH_3$-3-Py-$(CH_2)_2$— An example of a compound containing this moiety is dimebon.

In another variation, $R^3$ is hydrogen. In other variations, $R^3$ is any one of the alkyl groups noted for $R^1$ above, the same as if each and every alkyl variation listed for $R^1$ is separately and individually listed for R. In another variation, $R^3$ is a halo group. In another variation, $R^3$ is hydrogen or an alkyl group. In another variation, $R^3$ is a halo or alkyl group. In another variation, $R^3$ is hydrogen or a halo group. In another variation, $R^3$ is selected from the group consisting of hydrogen, alkyl and halo. In another variation, $R^3$ is Br. In another variation, $R^3$ is I. In another variation, $R^3$ is F. In another variation, $R^3$ is Cl.

In another variation, the compound is of the Formula (A) and $R^1$ is selected from a lower alkyl or benzyl; $R^2$ is selected from a hydrogen, benzyl or 6-$CH_3$-3-Py-$(CH_2)_2$ and R is selected from hydrogen, lower alkyl or halo, or any pharmaceutically acceptable salt thereof. In another variation, $R^1$ is selected from $CH_3$, $CH_3CH_2$, or benzyl; $R^2$ is selected from H, benzyl, or 6-$CH_3$-3-Py-$(CH_2)_2$; and $R^3$ is selected from H, $CH_3$ or —Br, or any pharmaceutically acceptable salt thereof. In another variation the compound is selected from the group consisting of: cis(±)2,8-dimethyl-2,3,4,4a,5,9b-hexahydro-1H-pyrido[4,3-b]indole as a racemic mixture or in the substantially pure (+) or substantially pure (−) form; 2-ethyl-2,3,4,5-tetrahydro-1H-pyrido[4,3-b]indole; 2-benzyl-2,3,4,5-tetrahydro-1H-pyrido[4,3-b]indole; 2,8-dimethyl-5-benzyl-2,3,4,5-tetrahydro-1H-pyrido[4,3-b]indole; 2-methyl-5-(2-methyl-3-pyridyl)ethyl-2,3,4,5-tetrahydro-1H-pyrido[4,3-b]indole; 2,8-dimethyl-5-(2-(6-methyl-3-pyridyl)ethyl)-2,3,4,5-tetrahydro-1H-pyrido[4,3-b]indole; 2-methyl-2,3,4,5-tetrahydro-1H-pyrido[4,3-b]indole; 2,8-dimethyl-2,3,4,5-tetrahydro-1H-pyrido[4,3-b]indole; or 2-methyl-8-bromo-2,3,4,5-tetrahydro-1H-pyrido[4,3-b]indole or any pharmaceutically acceptable salt of any of the foregoing.

In another variation, the compound is of the formula (A) wherein $R^1$ is $CH_3$, $R^2$ is H and $R^3$ is —$CH_3$ or any pharmaceutically acceptable salt thereof. The compound may be of the Formula (A) where $R^1$ is $CH_3CH_2$ or benzyl, $R^2$ is H, and $R^3$ is $CH_3$ or any pharmaceutically acceptable salt thereof. The compound may be of the Formula (A) where $R^1$ is $CH_3$, $R^2$ is benzyl, and $R^3$ is —$CH_3$ or any pharmaceutically acceptable salt thereof. The compound may be of the Formula (A) where $R^1$ is —$CH_3$, $R^2$ is 6-$CH_3$-3-Py-$(CH_2)_2$—, and $R^3$ is —H or any pharmaceutically acceptable salt thereof. The compound may be of the Formula (A) where $R^2$ is 6-$CH_3$-3-Py-$(CH_2)_2$— or any pharmaceutically acceptable salt thereof. The compound may be of the Formula (A) where $R^1$ is —$CH_3$, $R^2$ is —H, and $R^3$ is —H or —$CH_3$ or any pharmaceutically acceptable salt, thereof. The compound may be of the Formula (A) where $R^1$ is —$CH_3$, $R^2$ is —H, and $R^3$ is —Br, or any pharmaceutically acceptable salt thereof. The compound may be of the Formula (A) where $R^1$ is selected from a lower alkyl or arylalkyl, $R^2$ is selected from a hydrogen, arylalkyl or substituted heteroarylalkyl and $R^3$ is selected from hydrogen, lower alkyl or halo.

In another embodiment, dimebolins of formula (B)

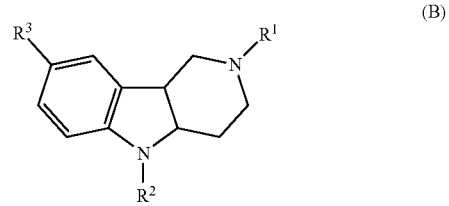

(B)

or a pharmaceutically acceptable salt thereof are described, wherein $R^1$ is alkyl or arylalkyl; $R^2$ is hydrogen, benzyl, or 6-methylpyridinyl-3-ethyl; $R^3$ is hydrogen, alkyl, or halo; and bond (a) is a single bond or a double bond.

In another embodiment, dimebolins of formula (B) are described wherein $R^1$ is methyl, ethyl or benzyl. In another embodiment, dimebolins of formula (B) are described wherein $R^2$ is hydrogen, benzyl, or 6-methylpyridinyl-3-ethyl. In another embodiment, dimebolins of formula (B) are described wherein $R^3$ is hydrogen, methyl, or bromo. In another embodiment, dimebolins of formula (B) are described wherein $R^1$ and $R^3$ are each methyl; and $R^2$ is hydrogen. In another embodiment, dimebolins of formula (B) are described wherein the ring fusion is cis. In another embodiment, dimebolins of formula (B) are described in a pharmaceutically acceptable quaternary salt form.

In another embodiment, dimebolins of formula (C)

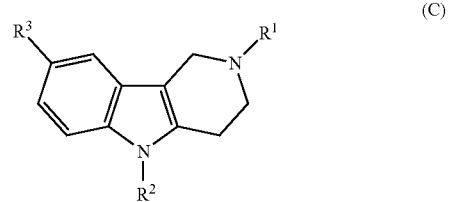

(C)

or a pharmaceutically acceptable salt thereof are described, wherein $R^1$ is alkyl or arylalkyl; $R^2$ is hydrogen, benzyl, or 6-methylpyridinyl-3-ethyl; $R^3$ is hydrogen, alkyl, or halo; and bond (a) is a single bond or a double bond.

In another embodiment, dimebolins of formula (C) are described wherein $R^1$ is methyl, ethyl or benzyl. In another embodiment, dimebolins of formula (C) are described wherein $R^2$ is hydrogen, benzyl, or 6-methylpyridinyl-3-ethyl. In another embodiment, dimebolins of formula (C) are described wherein $R^3$ is hydrogen, methyl, or bromo.

In another embodiment, dimebolins of formula (C) are described wherein $R^1$ is ethyl or benzyl; and $R^2$ and $R^3$ are each hydrogen; or $R^1$ and $R^3$ are each methyl; and $R^2$ is benzyl; or $R^1$ is methyl; $R^2$ is 6-methylpyridinyl-3-ethyl; and $R^3$ is hydrogen; or $R^1$ and $R^3$ are each methyl; and $R^2$ is 6-methylpyridinyl-3-ethyl; or $R^1$ is methyl; $R^2$ is hydrogen; and $R^3$ is hydrogen or methyl; or $R^1$ is methyl; $R^2$ is hydrogen; and $R^3$ is bromo. In another embodiment, dimebolins of formula (C) are described in a pharmaceutically acceptable quaternary salt form.

Additional illustrative dimebolins that may included in the compositions and methods described herein include hydrogenated pyrido [4,3-b] indoles of the formula (D) or the formula (E):

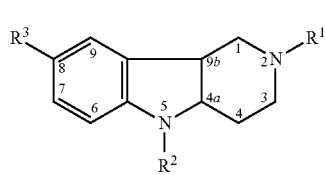
(D)

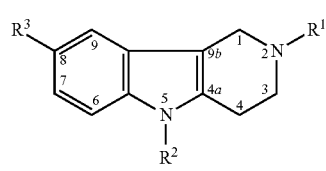
(E)

and pharmaceutically acceptable salts thereof

For compounds of a general formulae (D) or (E), $R^1$ represents $CH_3$, $CH_3CH_2$, or $PhCH_2$ (benzyl); $R^2$ is H, $PhCH_2$, or $6CH_3$-3-Py-$(CH_2)_2$; $R^3$ is H, $CH_3$, or Br, in any combination of the above substituents. All possible combinations of the substituents of formulae (D) or (E) are described herein as specific and individual compounds the same as if each single and individual compound were listed by chemical name. Also contemplated are the compounds of formulae (D) or (E), with any deletion of one or more possible moieties from the substituent groups listed above, such as for example where $R^1$ represents $CH_3$. In one variation, $R^2$ is H, $PhCH_2$, or $6CH_3$-3-Py-$(CH_2)_2$; and $R^3$ is H, $CH_3$, or Br, or where $R^1$ represents $CH_3$; $R^2$ is $6CH_3$-3-Py-$(CH_2)_2$; and $R^3$ represents H, $CH_3$, or Br.

The compound may be formula (D), where $R^1$ is $CH_3$, $R^2$ is H, and $R^3$ is $CH_3$. The compound may be formula (E), where $R^1$ is represented by $CH_3$, $CH_3CH_2$, or $PhCH_2$; $R^2$ is H, $PhCH_2$, or $6CH_3$-3-Py-$(CH_2)_2$; $R^3$ is H, $CH_3$, or Br. The compound may be formula (E), where $R^1$ is $CH_3CH_2$ or $PhCH_2$, $R^2$ is H, and $R^3$ is H; or a compound, where $R^1$ is $CH_3$, $R^2$ is $PhCH_2$, $R^3$ is $CH_3$; or a compound, where $R^1$ is $CH_3$, $R^2$ is $6$-$CH_3$-3-Py-$(CH_2)_2$, and $R^3$ is $CH_3$; or a compound, where $R^1$ is $CH_3$, $R^2$ is H, $R^3$ is H or $CH_3$; or a compound, where $R^1$ is $CH_3$, $R^2$ is H, $R^3$ is Br.

In another embodiment, the methods and compositions include a therapeutically effective amount of a dimebolin of the formula

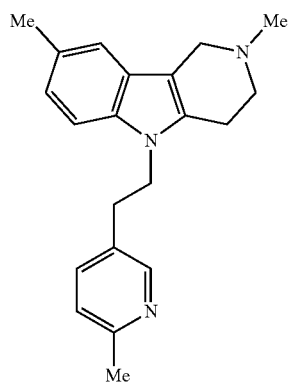 [SMILES: Cc1ccc2c(c1)c1c(n2CCc2ccc(C)nc2)CCN(C)C1]

or a pharmaceutically acceptable salt, such as the hydrochloride salt.

Additional illustrative dimebolins that may included in the compositions and methods described herein include hydrogenated pyrido[4,3-b]indoles or pharmaceutically acceptable salts thereof, such as an acid or base salt thereof. A hydrogenated pyrido[4,3-b]indole can be a tetrahydropyrido[4,3-b]indole or pharmaceutically acceptable salt thereof. The hydrogenated pyrido[4,3-b]indole can also be a hexahydropyrido[4,3-b]indole or pharmaceutically acceptable salt thereof. The hydrogenated pyrido[4,3-b]indole compounds can be substituted with 1 to 3 substituents, although unsubstituted hydrogenated pyrido[4,3-b]indole compounds or hydrogenated pyrido[4,3-b]indole compounds with more than 3 substituents are also contemplated. Suitable substituents include but are not limited to alkyl, lower alkyl, arylalkyl, heteroarylalkyl, substituted heteroarylalkyl, substituted arylalkyl, and halo.

The hydrogenated pyrido[4,3-b]indoles can be in the form of pharmaceutically acceptable salts thereof. The pharmaceutically acceptable salts include pharmaceutically acceptable acid salts. Examples of particular pharmaceutically acceptable salts include hydrochloride salts or dihydrochloride salts. In a particular variation, the hydrogenated pyrido [4,3-b]indole is a pharmaceutically acceptable salt of 2,8-dimethyl-5-(2-(6-methyl-3-pyridyl)ethyl)-2,3,4,5-tetrahydro-1H-pyrido[4,3-b]indole, such as 2,8-dimethyl-5-(2-(6-methyl-3-pyridyl)ethyl)-2,3,4,5-tetrahydro-1H-pyrido [4,3-b]indole dihydrochloride (dimebon). In another embodiment, the dimebolins are selected from 2-methyl-2, 3,4,5-tetrahydro-1H-pyrido[4,3-b]indole; 2,8-dimethyl-2,3, 4,5-tetrahydro-1H-pyrido[4,3-b]indole, or its methyliodide; cis-(±) 2,8-dimethyl-2,3,4,4a,5,9b-hexahydro1H-pyrido[4, 3-b]indole, or its dihydrochloride; 2-methyl-8-bromo-2,3,4, 5-tetrahydro-1H-pyrido[4,3-b]indole, or its hydrochloride; 2-ethyl-2,3,4,5-tetrahydro-1H-pyrido[4,3-b]indole; 2-benzyl-2,3,4,5-tetrahydro-1H-pyrido[4,3-b]indole; 2,8-dimethyl-5-benzyl-2,3,4,5-tetrahydro-1H-pyrido[4,3-b]indole, or its hydrochloride; 2-methyl-5-[2-(6-methyl-3-pyridyl) ethyl]-2,3,4,5-tetrahydro-1H-pyrido[4,3-b]indole, or its sesquisulfate monohydrate; and 2,8-dimethyl-5-[2-(6-methyl-3-pyridyl)ethyl]-2,3,4,5-tetrahydro-1H-pyrido[4,3-b]indole, or its dihydrochloride.

Additional illustrative dimebolins that may included in the compositions and methods described herein include cis(±) 2,8-dimethyl-2,3,4,4a,5,9b-hexahydro-1H-pyrido[4, 3-b]indole and its dihydrochloride; 2-ethyl-2,3,4,5-tetrahydro-1H-pyrido[4,3-b]indole; 2-benzyl-2,3,4,5-tetrahydro-1H-pyrido[4,3-b]indole; 2,8-dimethyl-5-benzyl-2,3,4,5-tetrahydro-1H-pyrido[4,3-b]indole and its dihydrochloride;

2-methyl-5-(2-methyl-3-pyridyl)ethyl-2,3,4,5-tetrahydro-1H-pyrido[4,3-b]indole and its sesquisulfate; 2,8-dimethyl-5-(2-(6-methyl-3-pyridyl)ethyl)-2,3,4,5-tetrahydro-1H-pyrido[4,3-b]indole and its dihydrochloride (dimebon); 2-methyl-2,3,4,5-tetrahydro-1H-pyrido[4,3-b]indole; 2,8-dimethyl-2,3,4,5-tetrahydro-1H-pyrido[4,3-b]indole and its methyl iodide; 2-methyl-8-bromo-2,3,4,5-tetrahydro-1H-pyrido[4,3-b]indole and its hydrochloride.

In a another variation, the hydrogenated pyrido[4,3-b]indole is 2,8-dimethyl-5-(2-(6-methyl-3-pyridyl)ethyl)-2,3,4,5-tetrahydro-1H-pyrido[4,3-b]indole or a pharmaceutically acceptable salt thereof. The compound for use in the compositions and methods may be 2,8-dimethyl-5-(2-(6-methyl-3-pyridyl)ethyl-2,3,4,5-tetrahydro-1H-pyrido[4,3-b]indole or any pharmaceutically acceptable salt thereof, such as an acid salt, a hydrochloride salt or a dihydrochloride salt thereof.

In each of the foregoing and following embodiments, it is to be understood that the formulae include and represent not only all pharmaceutically acceptable salts of the dimebolins, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non crystalline and/or amorphous forms of the compounds.

Dimebolins may be prepared according to Horlein, Chem. Ber., 1954, Bd. 87, hft 4, p. 463-472; Cattanach et al, J. Chem. Soc. (ser. C) 1968, 1235-1243; Yurovskaya and Rodionov, Khim. Geterots. Soed., 1981, No. 8, p. 1072-1078; Yakhontov and Glushkova, Synthatic Drugs (edited by A. G. Natradze), Moscow, "Meditsina Publishers", 1983, p. 234-237; Buu-Hoi et al., J. Chem. Soc, 1964, No. 2, p. 708-711; Kucherova and Kochetkov, J. Obshch. Khim., 1956, v. 26, p. 3149-3154; and Kost et al., "Khim. Geterots. Soed.", 1973, No. 2, p. 207-212; Yakhontov, L. N., Glushkov, R. G, Synthetic Therapeutic Drugs; A. G Natradze, Ed., Moscow Medicina, 1983, p. 234-237; CJ. Cattanach, A. Cohen & B. H. Brown, J. Chem. Soc. (Ser. C) 1968, p. 1235-1243; N. P. Buu-Hoi, O. Roussel, P. Jacquignon, J. Chem. Soc, 1964, N 2, p. 708-711; N. F. Kucherova and N. K. Kochetkov (General Chemistry (Russ.), 1956, 26:3149-3154); A. N. Kost, M. A. Yurovskaya, T. V. Mel'nikova, in Chemistry of Heterocyclic Compounds, 1973, N 2, p. 207-212; U, Horlein in Chem. Ber., 1954, Bd. 87, hft 4, 463-p. 472; and M. Yurovskaya and LL. Rodionov in Chemistry of Heterocyclic Compounds (1981, N 8, p. 1072-10). It is to be understood that when bond (a) is a single bond, such dimebolins include two stereocenters in the pyrido[4,3-b]indole ring structure (e.g., carbons 4a and 9b of formula (A)), which can adopt a cis or a trans ring fusion. A composition may comprise such a compound in substantially pure form, such as a composition of substantially pure (S,S), (R,R), (S,R), or (R,S) compound. A composition of substantially pure compound generally means that the composition contains no more than 15% or no more than 10% or no more than 5% or no more than 3% or no more than 1% impurity of the compound in a different stereochemical form. For instance, a composition of substantially pure (S, S) compound generally means that the composition contains no more than 15% or no more than 10% or no more than 5% or no more than 3% or no more than 1% of the R,R or S,R or R,S form of the compound. A composition may contain the compound as mixtures of such stereoisomers, where the mixture may be enantiomers, for example (S,S) and (R,R), or diastereomers, for example (S, S) and (R,S) or (S,R), in equal or unequal amounts. A composition may contain the compound as a mixture of 2 or 3 or 4 such stereoisomers in any ratio of stereoisomers. Compounds disclosed herein having stereocenters other than in the pyrido[4,3-b]indole ring structure intends all stereochemical variations of such compounds, including but not limited to enantiomers and diastereomers in any ratio, and includes racemic and enantioenriched and other possible mixtures. Unless stereochemistry is explicitly indicated in a structure, the structure is intended to embrace all possible stereoisomers of the compound depicted, either alone or as mixtures.

In another embodiment of the compositions, kits, packages, and methods and uses described herein, one or more CoQ10 and analogs and derivatives thereof, such as idebenone, are included with the one or more tetracyclic pyrazinoindoles.

In another embodiment, compositions and methods are described herein that also include CoQ10 and analogs, such as idebenone. In another embodiment, one or more tetracyclic pyrazinoindoles described herein are co-administered with a CoQ10 analog, such as idebenone. Accordingly, the co-administration of one or more CoQ10 analogs capable of further reducing cell damage, such as may be caused by Reactive Oxygen Species of mitochondrial dysfunction, may be beneficial as a co-therapy with the administration of pirlindoles as described herein.

It is to be understood that in any of the method or composition embodiments described herein, the corresponding acid addition salt of any compound may be administered in addition to or instead of the corresponding neutral compound. Illustrative acid salts may be formed from, but at not limited to, inorganic acids and/or organic acids. In addition, it is to be understood that bis salts may be formed and administered, such as the dihydrochloride acid salt, and the like.

As used herein, the term "alkyl" includes a chain of carbon atoms, which is optionally branched. It is to be understood that alkyl is advantageously of limited length, including $C_1$-$C_{24}$, $C_1$-$C_{12}$, $C_1$-Cg, $C_1$-$C_6$, and $C_1$-$C_4$. It is appreciated herein that shorter alkyl groups add less lipophilicity to the compound and accordingly will have different pharmacokinetic behavior. As used herein, the term "cycloalkyl" includes a chain of carbon atoms, which is optionally branched, and where at least a portion of the chain in cyclic. It is to be understood that chain forming cycloalkyl is advantageously of limited length, including $C_3$-$C_{24}$, $C_3$-$C_{12}$, $C_3$-Cg, $C_3$-$C_6$, and $C_3$-$C_4$. It is appreciated herein that shorter alkyl groups add less lipophilicity to the compound and accordingly will have different pharmacokinetic behavior. As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "heterocyclyl" including heterocycle includes a chain of atoms that includes both carbon and at least one heteroatom, and is optionally branched, where at least a portion of the chain is cyclic. Illustrative heteroatoms include nitrogen, oxygen, and sulfur. In certain variations, illustrative heteroatoms also include phosphorus, and selenium. Illustrative heterocycles include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic and aromatic heterocyclic groups, each of which may be optionally substituted. As used herein, the term "heteroaryl" includes aromatic heterocyclic groups, each of which may be optionally substituted. Illustrative carbocyclic aromatic groups described herein include, but are not limited to, phenyl, naphthyl, and the like. Illustrative heterocyclic aromatic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "optionally substituted amino" includes derivatives of amino as described herein, such as, but not limited to, acylamino, urea, and carbamate, and the like.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like.

The term "optionally substituted aryl" as used herein includes the replacement of hydrogen atoms with other functional groups on the aryl that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like.

Illustrative substituents include, but are not limited to, a radical —$(CH_2)_mZ$, where m is an integer from 0-6 and Z is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-Cg cycloalkyl, cycloalkoxy, including $C_3$-Cg cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-Cg halocycloalkyl, halocycloalkoxy, including $C_3$-Cg halocycloalkoxy, amino, $C_1$-$C_6$ alkylamino, ($C_1$-$C_6$ alkyl)(Ci-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)(Ci-$C_6$ alkyl) aminoalkyl, alkylcarbonylaminoalkyl, N—($C_1$-$C_6$ alkyl) alkylcarbonylaminoalkyl, cyano, and nitro; or Z is selected from —$CO_2R^4$ and —$CONR^5R^6$, where $R^4$, $R^5$, and $R^6$ are each independently selected in each occurrence from hydrogen, $C_1$-$C_6$ alkyl, and aryl-CrCβ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —$CO_2H$, —$NR_2$. Illustrative prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylamino alkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, ($C_3$-$C_{20}$)alkanoyl; halo-($C_3$-$C_{20}$)alkanoyl; ($C_3$-$C_{20}$)alkenoyl; ($C_4$-$C_7$)cycloalkanoyl; ($C_3$-$C_6$)-cycloalkyl($C_2$-$Ci_6$)alkanoyl; optionally substituted aroyl, such as unsubstituted aroyl or aroyl substituted by 1 to 3 substituents selected from the group consisting of halogen, cyano, trifluoromethanesulphonyloxy, (Ci-$C_3$)alkyl and (Ci-$C_3$)alkoxy, each of which is optionally further substituted with one or more of 1 to 3 halogen atoms; optionally substituted aryl($C_2$—$Ci_6$)alkanoyl, such as the aryl radical being unsubstituted or substituted by 1 to 3 substituents selected from the group consisting of halogen, (Ci-$C_3$)alkyl and (Ci-$C_3$)alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, (Ci-$C_3$)alkyl, and (Ci-$C_3$)alkoxy, each of which is optionally further substituted with 1 to 3 halogen atoms. The groups illustrated are exemplary, not exhaustive, and may be prepared by conventional processes. It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

In addition, in those embodiments described herein drawn to combination therapy comprising administration of tetracyclic pyrazinoindoles, and/or one or more dimebolins, and/or one or more CoQ10 analogs, and the like, "therapeutically effective amount" refers to that amount of the combination of agents taken together so that the combined effect elicits the desired biological or medicinal response. For example, the therapeutically effective amount of pirlindole and dimebon, pirlindole and idebenone, and the like, would be the amount of each of pirlindole and of dimebon, or the amount of each of pirlindole and of idebenone, and the like that when taken together or sequentially have a combined effect that is therapeutically effective. Further, it is appreciated that in some embodiments of such methods that include co-administration, the amount of tetracyclic pyrazinoindoles, dimebon, and/or idebenone, and the like, when taken individually may or may not be therapeutically effective. It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein.

Illustratively, compositions may include one or more carriers, diluents, and/or excipients. The compounds described herein, or compositions containing them, may be formulated in a therapeutically effective amount in any conventional dosage forms appropriate for the methods described herein, and include one or more carriers, diluents, and/or excipients therefor. Such formulation compositions may be administered by a wide variety of conventional routes for the methods described herein, and in a wide variety of dosage formats, utilizing known procedures. See generally, Remington: The Science and Practice of Pharmacy, ($21^{st}$ ed., 2005).

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, and rectal in dosage form unit formulations containing conventional nontoxic pharmaceutically-acceptable carriers, adjuvants and vehicles. Compounds may also be administered directly to the nervous system including, but not limited to, intracerebral, intraventricular, intracerebro ventricular, intrathecal, intracisternal, intraspinal and/or perispinal routes of administration by delivery via intracranial or intravertebral needles and/or catheters with or without pump devices.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

In addition to the foregoing illustrative dosages and dosing protocols, it is to be understood that an effective amount of any one or a mixture of the compounds described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

In making the pharmaceutical compositions of the compounds described herein, a therapeutically effective amount of one or more compounds in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the formulation compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The compositions may contain anywhere from about 0.1% to about 99.9% active ingredients, depending upon the selected dose and dosage form. The formulations can additionally include lubricating agents; wetting agents; emulsifying and suspending agents; preserving agents; sweetening agents; and flavoring agents. The compositions can be formulated so as to provide quick, sustained or delayed release of the active ingredient after administration to the patient. It is appreciated that the carriers, diluents, and excipients used to prepare the compositions described herein are advantageously GRAS (Generally Regarded as Safe) compounds.

Tablet formulations may be uncoated or they may be coated using conventional techniques, such as that described in Encyclopedia of Pharmaceutical Technology, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating).

Illustrative sustained release formulations are described in U.S. Pat. Nos. 3,847,770; 3,916,899; 3,536,809; 3,598,123; 3,630,200; 4,008,719; 4,687,610; 4,769,027; 5,674,533; 5,059,595; 5,591,767; 5,120,548; 5,073,543; 5,639,476; 5,354,566; and 5,733,566, the disclosures of which are incorporated herein by reference.

The pharmaceutical composition may also be administered parenterally by injection, infusion or implantation. Suitable routes for parenteral administration include intravenous, intraarterial, intraperitoneal, epidurial, intraurethral, intrasternal, intramuscular and subcutaneous, as well as any other conventional routes of parenteral administration. Suitable means of parenteral administration include needle (including microneedle) injectors, needle-free injectors and infusion techniques, as well as any other means of parenteral administration. Parenteral formulations are typically aqueous solutions which may contain excipients such as salts, carbohydrates and buffering agents (preferably at a pH in the range from about 3 to about 9), but, for some applications, they may be more suitably formulated as a sterile nonaqueous solution or as a dried form to be used in conjunction with a suitable vehicle such as sterile, pyrogen-free water. The preparation of parenteral formulations under sterile conditions, for example, by lyophilization, may readily be accomplished using conventional pharmaceutical techniques, such as is described in Remington: The Science and Practice of Pharmacy.

The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

The effective use of the methods described herein for treating or ameliorating FRDA, LHON, DAD, Leigh's disease, NARP, MNGIE, MERRF, MELAS, and the like may be based upon cellular models, such as model of primary human fibroblasts. For example, it is understood that FRDA, LHON, DAD, Leigh's disease, NARP, MNGIE, MERRF, MELAS, and the like in humans may be characterized by neurodegeneration, which can be seen in primary human fibroblasts harvested from patients suffering from these diseases. Illustrative cellular models of Friedreich's ataxia that may be used to evaluate the methods of treatment and the pharmaceutical compositions described herein to determine the therapeutically effective amounts described herein, include but not limited to the primary human fibroblasts harvested from patients suffering from Friedreich's ataxia, in which depletion of antioxidant defenses is induced by pre-treatment with L-buthionine-S,R-sulfoximine (BSO), an inhibitor of GSH biosynthesis. Cellular models of the mitochondrial diseases that may be used to evaluate the methods of treatment and the pharmaceutical compositions described herein include but not limited to the primary human fibroblasts harvested from patients suffering from LHON, pre-treated with BSO in a similar manner.

The following examples further illustrate specific embodiments of the invention; however, the following illustrative examples should not be interpreted in any way to are to limit invention.

EXAMPLES

EXAMPLE. The following examples, and corresponding pharmaceutically acceptable salts thereof are described herein, and may be included in the methods and compositions described herein.

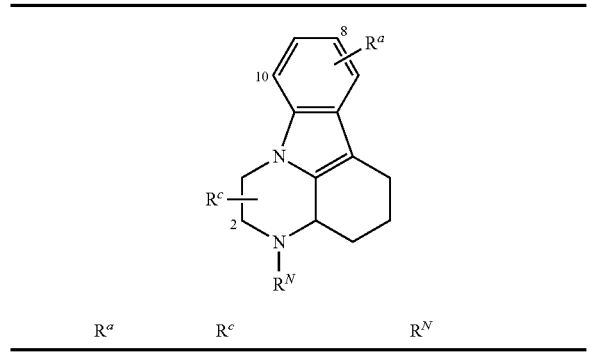

| $R^a$ | $R^c$ | $R^N$ |
|---|---|---|
| 8-Me | H | H |
| 8-OMe | H | Me |
| 8-cyclohexyl | H | H |
| 8-Me | H | Me$_2$(CH$_2$)$_4$NHCH$_2$CH(OH)CH$_2$ |
| 8-cyclohexyl | H | 3,4,5-trimethoxybenzoyl |
| 8-Br | H | n-Bu |
| 8-Me | H | CF$_3$(CF$_2$)$_5$C(O) |
| H | H | NH$_2$CH$_2$CH$_2$ |
| 8-(4-methoxyphenyl) | H | H |
| 8-Me | H | 3-methyl-1-piperidinyl-C(O)CH$_2$ |
| 8-cyclododecyl | H | H |
| 8-Me | H | Me |
| 8-cyclohexyl | H | PhCH=CHCH=NNHC(O)CH$_2$ |
| 8-Me | H | 4-methyl-1-piperazinyl-CH$_2$CH(OH)CH$_2$ |
| 8-Me | H | 4-(3,4-dimethoxyphenyl)thiazol-2-yl |
| 8-F | H | H |
| 8-cyclohexyl | H | 1-methyl-3-nitro-1H-1,2,4-triazol-5-yl |
| 8-(adamant-1-yl) | H | H |
| 8-Me | H | piperidin-1-yl-CH(OH)CH$_2$ |
| 8-CO$_2$Et | H | H |
| H | 2-Ph | H |
| 8-cyclohexyl | H | Et$_2$NCH$_2$C(O) |
| 6,8-dimethyl | H | H |
| 8-Me | H | 4-ethylpiperazin-1-yl-CH$_2$CH(OH)CH$_2$ |
| 8-Me | H | NCCH$_2$ |
| 8-Me | H | NH$_2$CH$_2$CH$_2$ |
| 8-cyclohexyl | H | Et$_2$NCH$_2$CH$_2$ |
| 8-Me | H | NH$_2$C(O)CH$_2$CH$_2$ |
| 8-Me | H | CH$_3$C(O)CH$_2$ |
| 8-Me | H | 2-fluorobenzoyl |
| 8-OAc | H | H |
| 8-Me | H | (i-Pr)$_2$NCH$_2$CH$_2$ |
| 8-C(O)NHNH$_2$ | H | H |
| 8-Me | H | (structure shown below) |

[structure: 1-Me, 2-Me indole with EtO$_2$C at 3, OMe at 5, and HN-C(O)-CH$_2^+$ at 4]

| 8-Me | H | t-BuOC(O)NHCH(i-Bu)C(O) |
| 8-Me | H | (S)—t-BuOC(O)NHCH(i-Bu)C(O) |
| 8-OMe | H | Me |
| 8-cyclohexyl | H | H |
| 8-Me | H | Me$_2$(CH$_2$)$_4$NHCH$_2$CH(OH)CH$_2$ |
| 8-cyclohexyl | H | 3,4,5-trimethoxybenzoyl |
| 8-Br | H | n-Bu |
| 8-Me | H | CF$_3$(CF$_2$)$_5$C(O) |
| H | H | NH$_2$CH$_2$CH$_2$ |
| 8-(4-methoxyphenyl) | H | H |

-continued

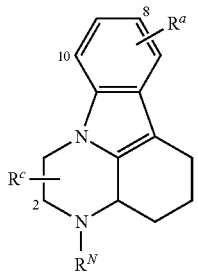

| $R^a$ | $R^c$ | $R^N$ |
|---|---|---|
| 8-Me | H | 3-methyl-1-piperidinyl-C(O)CH$_2$ |
| 8-cyclododecyl | H | H |
| 8-Me | H | Me |
| 8-cyclohexyl | H | PhCH=CHCH=NNHC(O)CH$_2$ |
| 8-Me | H | 4-methyl-1-piperazinyl-CH$_2$CH(OH)CH$_2$ |
| 8-Me | H | 4-(3,4-dimethoxyphenyl)thiazol-2-yl |
| 8-F | H | H |
| 8-cyclohexyl | H | 1-methyl-3-nitro-1H-1,2,4-triazol-5-yl |
| 8-(adamant-1-yl) | H | H |
| 8-Me | H | piperidin-1-yl-CH(OH)CH$_2$ |
| 8-CO$_2$Et | H | H |
| H | 2-Ph | H |
| 8-cyclohexyl | H | Et$_2$NCH$_2$C(O) |
| 6,8-dimethyl | H | H |
| 8-Me | H | 4-ethylpiperazin-1-yl-CH$_2$CH(OH)CH$_2$ |
| 8-Me | H | NCCH$_2$ |
| 8-Me | H | NH$_2$CH$_2$CH$_2$ |
| 8-cyclohexyl | H | Et$_2$NCH$_2$CH$_2$ |
| 8-Me | H | NH$_2$C(O)CH$_2$CH$_2$ |
| 8-Me | H | CH$_3$C(O)CH$_2$ |
| 8-Me | H | 2-fluorobenzoyl |
| 8-OAc | H | H |
| 8-Me | H | (i-Pr)$_2$NCH$_2$CH$_2$ |
| 8-C(O)NHNH$_2$ | H | H |
| 8-Me | H | (structure shown below) |

[structure: 1-Me, 2-Me indole with EtO$_2$C at 3, OMe at 5, and HN-C(O)-CH$_2^+$ at 4]

| 8-Me | H | t-BuOC(O)NHCH(i-Bu)C(O) |
| 8-Me | H | (S)—t-BuOC(O)NHCH(i-Bu)C(O) |
| 8-Me | H | Me$_2$N(CH$_2$)$_4$NHCH$_2$CH(OH)CH$_2$ |
| 8-Me | H | Et$_2$N(CH$_2$)$_3$NHCH$_2$CH(OH)CH$_2$ |

EXAMPLE. The following examples, and corresponding pharmaceutically acceptable salts thereof are described herein, and may be included in the methods and compositions described herein.

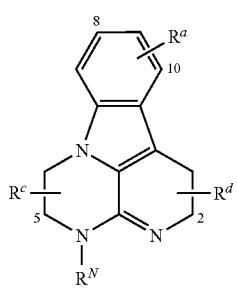

| $R^a$ | $R^c$ | $R^d$ | $R^N$ |
|---|---|---|---|
| 9-EtO | H | H | Me |
| 9-MeO | H | H | H |
| 9-MeO | H | H | n-propyl |
| 9-MeO | H | H | Me |
| 9-MeO | H | H | benzyl |
| H | H | H | Me |
| 9-F | H | H | Me |
| 9-MeO | H | H | cyclohexyl |
| 9-cyclohexyl | H | H | Me |
| 9-Me | H | H | Me |
| 9-hydroxy | H | H | Me |
| 7-MeO | H | H | Me |
| H | H | H | Et |
| 9-cyclohexyl | H | H | H |
| 9-n-PrO | H | H | Me |
| 8-MeO | H | H | Me |
| 9-benzyloxy | H | H | Me |
| H | 5-Me | H | Me |

EXAMPLE. The following examples, and corresponding pharmaceutically acceptable salts thereof are described herein, and may be included in the methods and compositions described herein.

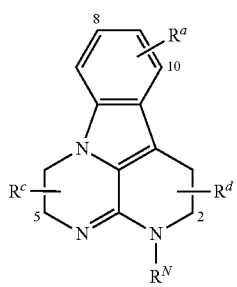

| $R^a$ | $R^c$ | $R^d$ | $R^N$ |
|---|---|---|---|
| 9-EtO | H | H | Me |
| 9-MeO | H | H | H |
| 9-MeO | H | H | n-propyl |
| 9-MeO | H | H | Me |
| 9-MeO | H | H | benzyl |
| H | H | H | Me |
| 9-F | H | H | Me |
| 9-MeO | H | H | cyclohexyl |
| 9-cyclohexyl | H | H | Me |
| 9-Me | H | H | Me |
| 9-hydroxy | H | H | Me |
| 7-MeO | H | H | Me |
| H | H | H | Et |
| 9-cyclohexyl | H | H | H |
| 9-n-PrO | H | H | Me |
| 8-MeO | H | H | Me |
| 9-benzyloxy | H | H | Me |
| H | 5-Me | H | Me |

EXAMPLE. The following examples, and corresponding pharmaceutically acceptable salts thereof are described herein, and may be included in the methods and compositions described herein.

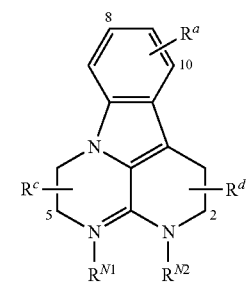

(I)

| $R^a$ | $R^c$ | $R^d$ | $R^{N1}$ | $R^{N2}$ |
|---|---|---|---|---|
| 9-EtO | H | H | Me | Me |
| 9-MeO | H | H | H | H |
| 9-MeO | H | H | n-propyl | n-propyl |
| 9-MeO | H | H | Me | Me |
| 9-MeO | H | H | benzyl | benzyl |
| 9-MeO | H | H | Me | benzyl |
| H | H | H | Me | Me |
| 9-F | H | H | Me | Me |
| 9-MeO | H | H | cyclohexyl | cyclohexyl |
| H | 5-Me | H | Me | Me |
| 9-cyclohexyl | H | H | Me | Me |
| 9-Me | H | H | Me | Me |
| 9-hydroxy | H | H | Me | Me |
| 7-MeO | H | H | Me | Me |
| H | H | H | Et | Et |
| 9-cyclohexyl | H | H | H | H |
| 9-n-PrO | H | H | Me | Me |
| 8-MeO | H | H | Me | Me |
| 9-benzyloxy | H | H | Me | Me |

EXAMPLE. Pirlindole, tetrindole, metralindole, or a combination thereof (50 mg) is administered two times daily to a patient suffering from or in need of relief from Friedreich's ataxia. Illustratively, the pirlindole in the form of tablets (comprising 25 mg of pirlindol, 30 mg of lactose, and 5 mg of magnesium stearate) for oral administration. The duration of treatment in this and other examples described herein is determined according to the progression of Friedreich's ataxia in each individual patient and dose adjustments are made accordingly. Treatment efficacy in this and other examples described herein is monitored by self-reporting and the results of treatment are evaluated statistically using Student's t-test and/or Fisher's "Fi" criterion.

EXAMPLE. Pirlindole, tetrindole, metralindole, or a combination thereof (50 mg) is administered two times daily to a patient suffering from or in need of relief from a mitochondrial disease. Illustratively, the pirlindole in the form of tablets (comprising 25 mg of pirlindol, 30 mg of lactose, and 5 mg of magnesium stearate) for oral administration. The duration of treatment in this and other examples described herein is determined according to the progression of the mitochondrial disease in each individual patient and dose adjustments are made accordingly. Treatment efficacy in this and other examples described herein is monitored by self-reporting and the results of treatment are evaluated statistically using Student's t-test and/or Fisher's "Fi" criterion.

EXAMPLE. Pirlindole, tetrindole, metralindole, or a combination thereof (100 mg) is administered two times daily to an adult or a child.

EXAMPLE. Pirlindole, tetrindole, metralindole, or a combination thereof (200 mg) is administered two times daily to an adult or a child.

EXAMPLE. Pirlindole, tetrindole, metralindole, or a combination thereof (250 mg) is administered two times daily to an adult.

EXAMPLE. Pirlindole, tetrindole, metralindole, or a combination thereof (400 mg) is administered two times daily to an adult.

EXAMPLE. Pirlindole, tetrindole, metralindole, or a combination thereof (25 mg) is administered three times daily to an adult or a child.

EXAMPLE. Pirlindole, tetrindole, metralindole, or a combination thereof (50 mg) is administered three times daily to an adult or a child.

EXAMPLE. Pirlindole, tetrindole, metralindole, or a combination thereof (100 mg) is administered three times daily to an adult or a child.

EXAMPLE. Pirlindole, tetrindole, metralindole, or a combination thereof (200 mg) is administered three times daily to an adult or a child.

EXAMPLE. Pirlindole, tetrindole, metralindole, or a combination thereof (250 mg) is administered three times daily to an adult.

EXAMPLE. Pirlindole, tetrindole, metralindole, or a combination thereof is administered as described herein, such as oral administration of 50 mg, two times daily, and coadministered with oral idebenone (150 mg tablet, Santhera) three times daily.

EXAMPLE. Pirlindole, tetrindole, metralindole, or a combination thereof is administered as described herein, such as oral administration of 50 mg, two times daily, and coadministered with oral alpha-lipoic acid 300 mg (Viale Europe) once daily.

EXAMPLE. Pirlindole, tetrindole, metralindole, or a combination thereof is administered as described herein, such as oral administration of 50 mg, two times daily, to a patient diagnosed with LHON, and co-administered with vitamin E (400 IU caps, Solgar) once daily.

EXAMPLE. Pirlindole, tetrindole, metralindole, or a combination thereof is administered as described herein, such as oral administration of 100 mg, two times daily, to a patient diagnosed with MELAS, and co-administered with oral vitamin C (100 mg Caps, Solgar) once daily. Treatment is started with 50 mg daily of pirlindole (one 25 mg tablet in the morning and one in the afternoon or evening) during the 1st week. In the 2nd week 100 mg per day (two tablets in the morning and two in the afternoon or evening) and in the 3rd week 150 mg per day (two tablets in the morning and four tablets in the afternoon or evening) is recommended. From the 4th week on, treatment can be continued with the recommended maintenance dose of 200 mg per day (four tablets twice a day).

EXAMPLE. Pirlindole, tetrindole, metralindole, or a combination thereof is administered as described herein, such as oral administration of 25 mg, two times daily, to a patient diagnosed with MERRF, and co-administered with oral thiamine (100 mg tablet, Galenica) two times daily.

EXAMPLE. Pirlindole, tetrindole, metralindole, or a combination thereof is administered as described herein, such as oral administration of 25 mg, two times daily, to a patient diagnosed with NARP, and co-administered with oral idebenone (150 mg tablet, Santhera) three times daily.

EXAMPLE. Pirlindole, tetrindole, metralindole, or a combination thereof is administered as described herein, such as oral administration of 25 mg, two times daily, to a patient diagnosed with MNGIE, and co-administered with oral thiamine (100 mg tablet, Galenica) two times daily.

EXAMPLE. Pirlindole, tetrindole, metralindole, or a combination thereof is administered as described herein, such as oral administration of 25 mg, two times daily, to a patient diagnosed with Leigh's disease, and co-administered with oral thiamine (100 mg tablet, Galenica) two times daily.

EXAMPLE. Pirlindole, tetrindole, metralindole, or a combination thereof is administered as described herein, such as oral administration of 50 mg, two times daily, to a patient diagnosed with DAD, and co-administered with vitamin E (400 IU caps, Solgar) once daily.

EXAMPLE. Tetracyclic pyrazinoindoles, and/or pharmaceutically acceptable salts thereof, including the compounds described herein, are efficacious in the primary human fibroblast cell line model of FRDA and LHON. Briefly, primary human fibroblasts from patients suffering from Friedreich's ataxia and LHON are lesioned with 100 µM BSO (LHON fibroblasts) or 250 µM BSO (FRDA fibroblasts) respectively, for 48 hours. Apoptosis, toxicity and viability rate of cells are determined using the ApoTox-Glo-Kit (Promega): the reagent for assessing viability and toxicity is applied 1:5 into treatment medium and incubated for 30 min at 37° C. Next, fluorescence is measured at the following wavelength sets: 400EX/505EM (viability) and 485EX/520EM (toxicity). In case of apoptosis measurement the caspase reagent was added 1:2 and incubated at RT for 30 min, the caspase activity (apoptosis) was measured as luminescence EXAMPLE. Evaluation of Tetracyclic Pyrazinoindoles, and Pharmaceutically Acceptable Salts Thereof. One or more tetracyclic pyrazinoindoles are applied 2 and 24 hours before BSO treatment and are present throughout the assay. An optional reference compound, such as idebenone may be included for comparison. BSO treated cells without any treatment (BSO group) as well as cells neither treated with BSO nor with any treatment (Vehicle Control (VC) group) serve as controls. Cells are assessed for apoptosis, toxicity and viability immediately after BSO lesion by means of the ApoTox-Glo-assay Kit (Promega). Three independent experiments in four technical replicates are performed for all groups as depicted in Table 1 (different tetracyclic pyrazinoindoles are labeled as Test Items (T.I.1-T.I.2) and an optional positive control Reference Item 1 (R.I.1)):

TABLE 1

Test items and doses

| Cells | Compound | Concentration(s) (µM) | Addition before lesion (hours) | Lesion (48 hours) |
|---|---|---|---|---|
| FRDA | pirlindole | 0.6, 1.8, 5.5, 16 | 2 | BSO |
| FRDA | pirlindole | 0.6, 1.8, 5.5, 16 | 24 | BSO |
| FRDA | tetrindole | 0.2, 0.6, 1.8, 5.5 | 2 | BSO |
| FRDA | tetrindole | 0.2, 0.6, 1.8, 5.5 | 24 | BSO |
| FRDA | idebenone | 1 | 2 | BSO |
| FRDA | idebenone | 1 | 24 | BSO |
| LHON | pirlindole | 0.6, 1.8, 5.5, 16 | 2 | BSO |
| LHON | pirlindole | 0.6, 1.8, 5.5, 16 | 24 | BSO |
| LHON | tetrindole | 0.2, 0.6, 1.8, 5.5 | 2 | BSO |
| LHON | tetrindole | 0.2, 0.6, 1.8, 5.5 | 24 | BSO |
| LHON | idebenone | 1 | 2 | BSO |
| LHON | idebenone | 1 | 24 | BSO |

The cells are assayed for apoptosis, overall cytotoxicity, and viability

BSO generally reduces a cell's protection against oxidative damage. Cells harvested from FRDA and LHON patients generate higher levels of ROS than normal cells. Apoptosis, toxicity and viability rate of cells are determined using the ApoTox-Glo-Kit (Promega): the reagent for assessing viability and toxicity is applied 1:5 into treatment medium and incubated for 30 min at 37° C. Next, fluorescence is measured at the following wavelength sets: 400EX/505EM (viability) and 485EX/520EM (toxicity). In case of apoptosis measurement the caspase reagent is added 1:2 and incubated at RT for 30 min, the caspase activity (apoptosis) was measured as luminescence Descriptive statistical analysis was performed. Data are presented as mean±standard error of mean (SEM) in percent of vehicle control, MPP+ lesion and BSO lesion, respectively. Differences between compound-treated groups and controls (vehicle, BSO) are evaluated by means of One-Way ANOVA.

Figure 1B:
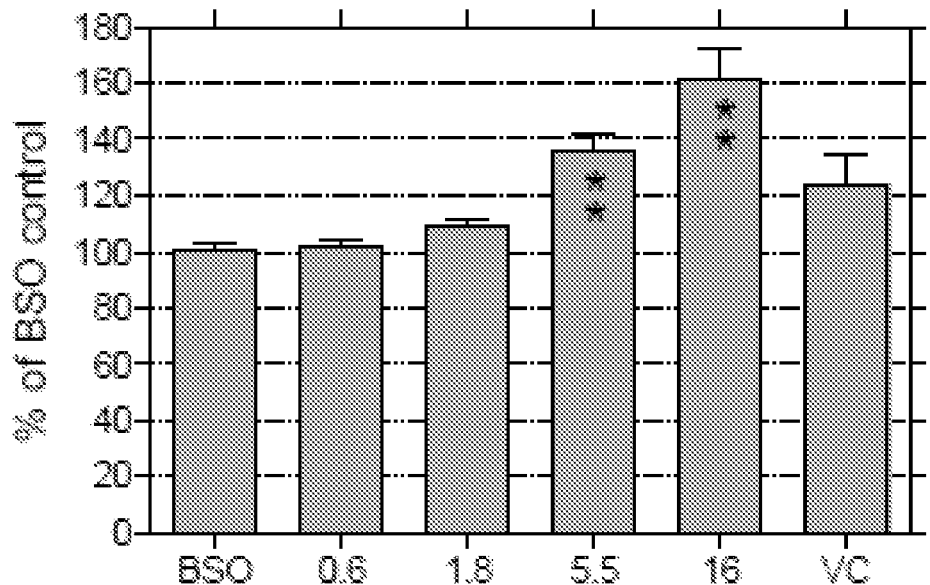

EXAMPLE. Pirlindole is diluted in water. One vial is thawed and administered 2 and 24 hours before BSO treatment, at concentrations 0.6 µM, 1.8 µM, 5.5 µM and 16 µM. Apoptosis, toxicity and viability rate of cells are determined using the ApoTox-Glo-Kit (Promega). Human primary fibroblasts from patients suffering from Friedreich's ataxia are used. Three independent experiments in four technical replicates are performed for all groups. The results are shown in FIGS. 1A and 1B. Graphs represent apoptosis and the viability effect of pirlindole (addition 2 and 24 h before lesion) on FRDA cells as % of the BSO lesion. The BSO lesion reduced cell viability by approximately 20% in FRDA cells compared to VC. In the BSO lesion assay Pirlindole exhibited a protective effect on cell viability from 1.8 to 16 µM (significant at 5.5, 16 µM) in a dose dependent manner in FRDA cells at both time points. The highest dose of 16 µM resulted in a 161% protective effect in relative cell viability ($p<0.001$). These data correlated with reduced apoptosis at a concentration of 16 µM of Pirlindole only after the short incubation (2 h before lesion). Statistically significant overall cytotoxicity over BSO control was not observed at any dose. Statistically significant improvement in apoptosis was not observed at any dose compared to the BSO group; however, there was not a statistically significant difference between the apoptosis observed at the highest dose of 16 and that observed in the VC treatment group ($p=0.98$). Statistical significance is indicated by NS=not significant $p>0.1$, *=$p<0.05$, =$p<0.01$, *=$p<0.001$ as determined by One-Way ANOVA. Data are shown as group mean+/−SEM.

Figure 2A:
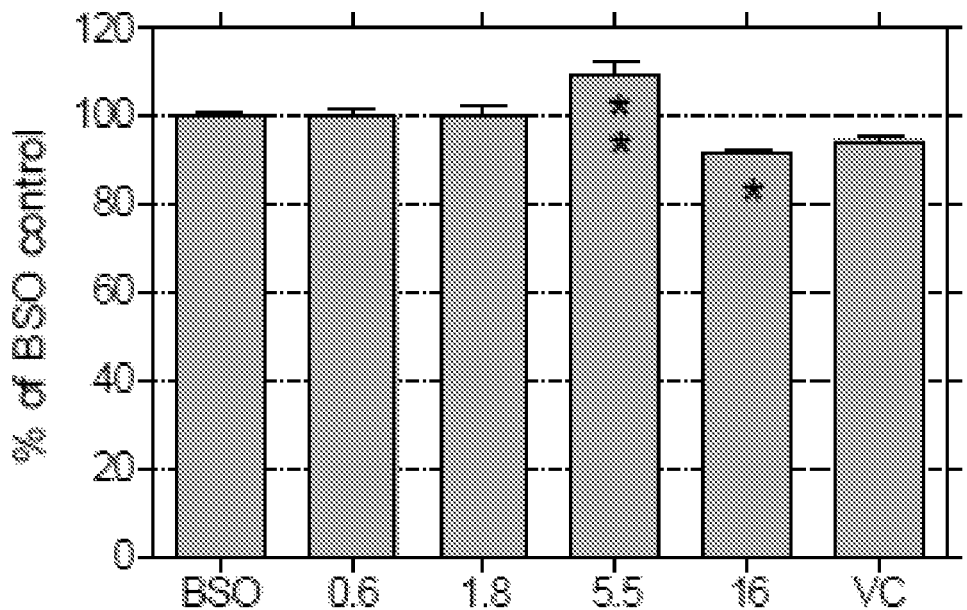
FIGS. 2A and 2B shows treatment with pirlindole of human primary fibroblasts from patients suffering from LHON. Cell apoptosis and viability effects of pirlindole (addition 24 h before lesion) on LHON cells as % of the BSO lesion are shown. Statistical significance is indicated by NS=not significant $p>0.1$, $*=p<0.05$, $=p<0.01$, $*=p<0.001$ as determined by One-Way ANOVA. Data are shown as group mean+/−SEM.
Figure 2B:
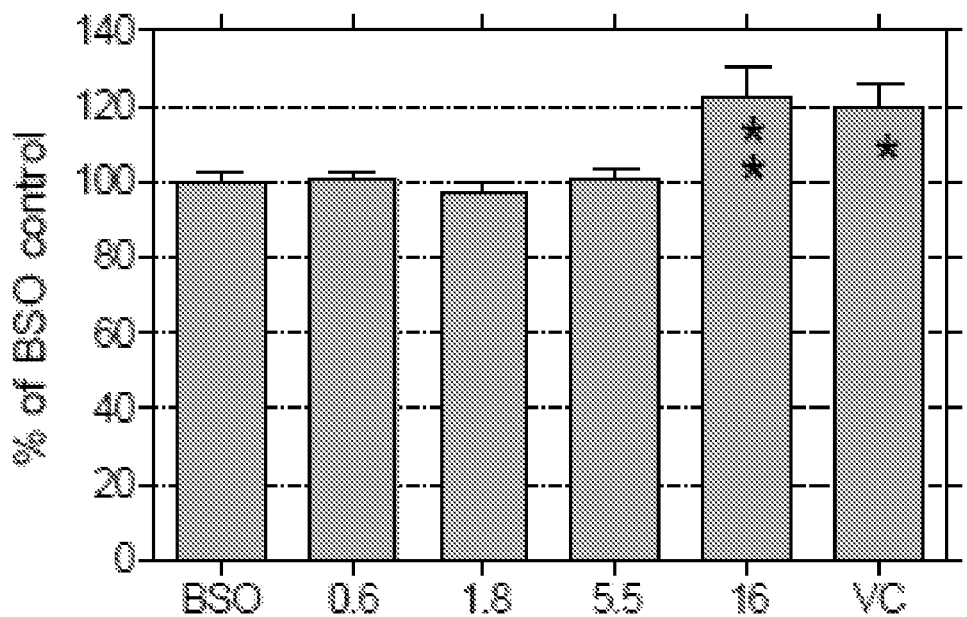

EXAMPLE. Pirlindole is diluted in water. One vial is thawed and administered 2 and 24 hours before BSO treatment, at concentrations 0.6 µM, 1.8 µM, 5.5 µM and 16 µM. Apoptosis, toxicity and viability rate of cells are determined using the ApoTox-Glo-Kit (Promega). Human primary fibroblasts from patients suffering from LHON are used. Three independent experiments in four technical replicates are performed for all groups. The results are shown in FIGS. 2A and 2B. Graphs represent apoptosis and viability effect of pirlindole (addition 2 and 24 h before lesion) on LHON cells as % of the BSO lesion. The BSO lesion reduced cell viability by approximately 20% in LHON cells compared to VC. In the BSO lesion assay pirlindole exhibited a protective effect on cell viability at 16 µM in LHON cells at both time points which correlated with reduced apoptosis and toxicity at this concentration (only significant after 24 h). The highest dose of 16 µM resulted in a 122% protective effect in relative cell viability ($p<0.05$). Statistically significant inferior apoptosis is observed at the 5.5 dose compared to the BSO group; however, there was not a statistically significant difference between the apoptosis observed at the 5.5 dose and that observed in the VC treatment group ($p=0.21$). Statistically significant overall cytotoxicity over BSO control was not observed at any dose. Statistical significance is indicated by NS=not significant $p>0.1$, *=$p<0.05$, =$p<0.01$, *=$p<0.001$ as determined by One-Way ANOVA. Data are shown as group mean+/−SEM.

Figure 3A:
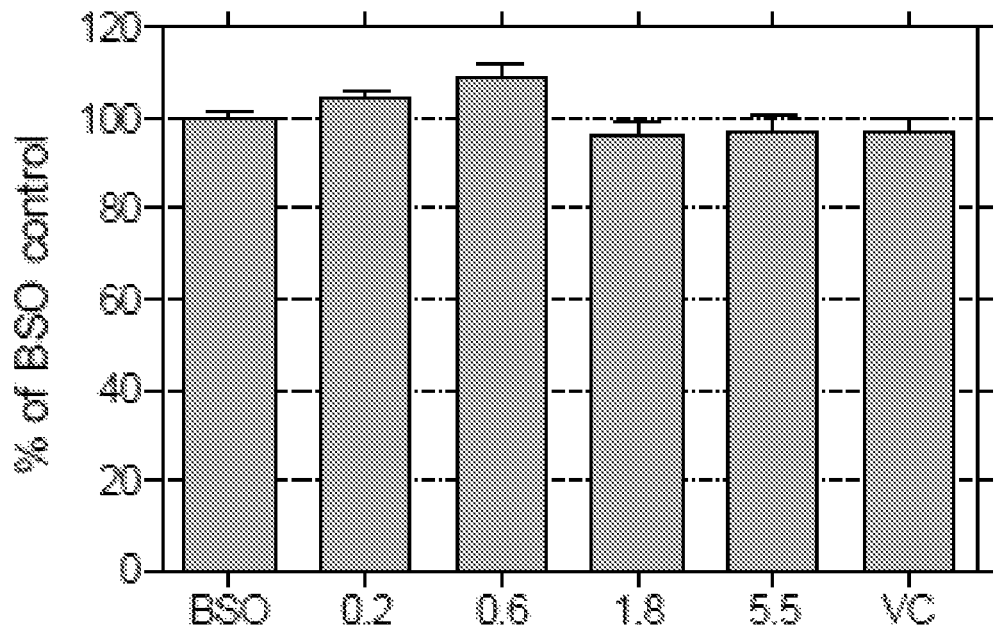
FIGS. 3A and 3B shows treatment with tetrindole of human primary fibroblasts from patients suffering from Friedreich's ataxia. Cell apoptosis and viability effects of tetrindole (addition 24 h before lesion) on FRDA cells as % of the BSO lesion are shown. Statistical significance is indicated by NS=not significant $p>0.1$, $*=p<0.05$, $=p<0.01$, $*=p<0.001$ as determined by One-Way ANOVA. Data are shown as group mean+/−SEM.
Figure 3B:
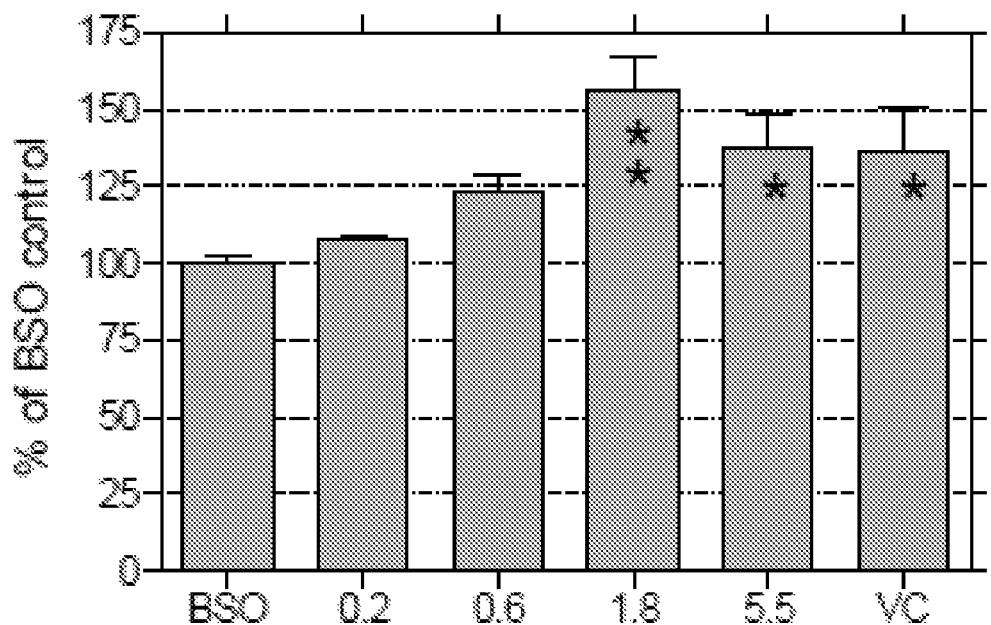

EXAMPLE. Tetrindole is diluted in DMSO. One vial is thawed and administered 2 and 24 hours before BSO treatment, at concentrations 0.2 µM, 0.6 µM, 1.8 µM and 5.5 µM. Apoptosis, toxicity and viability rate of cells are determined using the ApoTox-Glo-Kit (Promega). Human primary fibroblasts from patients suffering from Friedreich's ataxia are used. Three independent experiments in four technical replicates are performed for all groups. The results are shown in FIGS. 3A and 3B. Graphs represent apoptosis and viability effect of Pirlindole (addition 2 and 24 h before lesion) on FRDA cells as % of the BSO lesion. The BSO lesion reduced cell viability by approximately 20% in FRDA cells compared to VC. In the BSO lesion assay tetrindole exhibited a protective effect on cell viability from 0.2 to 5.5 µM (significant at 1.8 and also at 5.5 µM after 24 h) in a dose dependent manner in FRDA cells. The dose of 1.8 µM resulted in a 156% protective effect in relative cell viability ($p<0.05$). Tetrindole showed increased apoptosis (only after 2 h) and increased toxicity (only after 24 h) at a concentration of 5.5 µM. Statistically significant overall cytotoxicity over BSO control was not observed at any dose, except the highest dose of 5.5. However, there was not a statistical difference between the toxicity observed at the highest dose of 5.5 and that observed in the VC treatment group ($p=0.67$, NS). Statistically significant improvement in apoptosis was not observed at any dose compared to the BSO group. However, there was not a statistically significant difference between the apoptosis observed at the 1.8 dose ($p=0.51$) or the highest dose of 5.5 ($p=0.46$), and that observed in the VC treatment group. Statistical significance is indicated by NS=not significant $p>0.1$, *=$p<0.05$, =$p<0.01$, *=$p<0.001$ as determined by One-Way ANOVA. Data are shown as group mean+/−SEM.

Figure 4A:
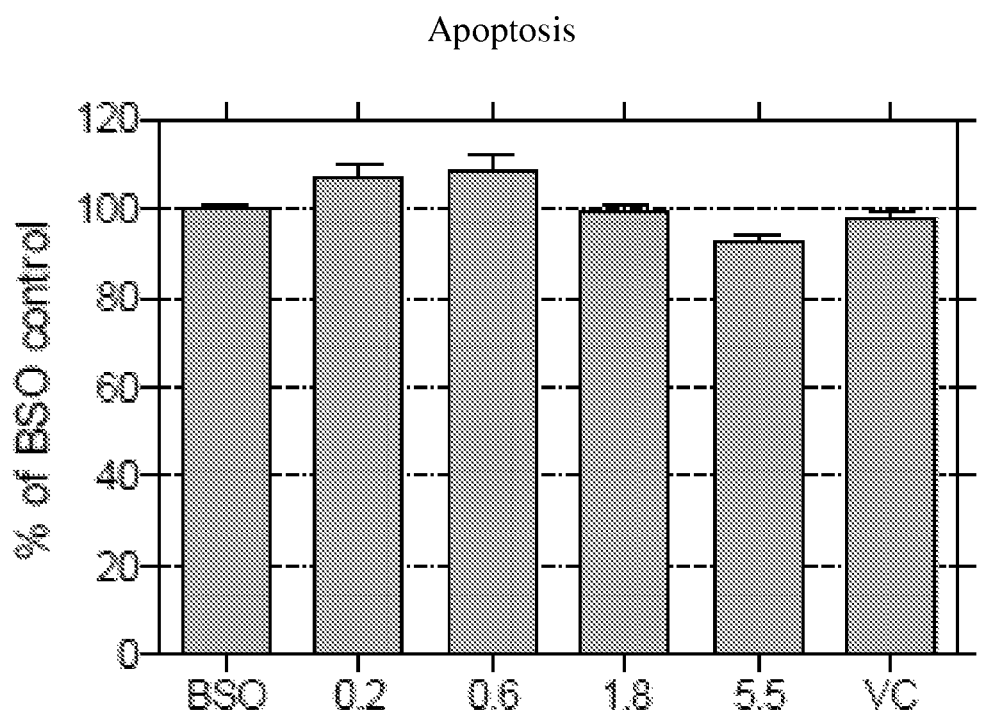
FIGS. 4A and 4B shows treatment with tetrindole of human primary fibroblasts from patients suffering from LHON. Cell apoptosis and viability effects of tetrindole (addition 24 h before lesion) on LHON cells as % of the BSO lesion are shown. Statistical significance is indicated by NS=not significant $p>0.1$, $*=p<0.05$, $=p<0.01$, $*=p<0.001$ as determined by One-Way ANOVA. Data are shown as group mean+/−SEM.
Figure 4B:
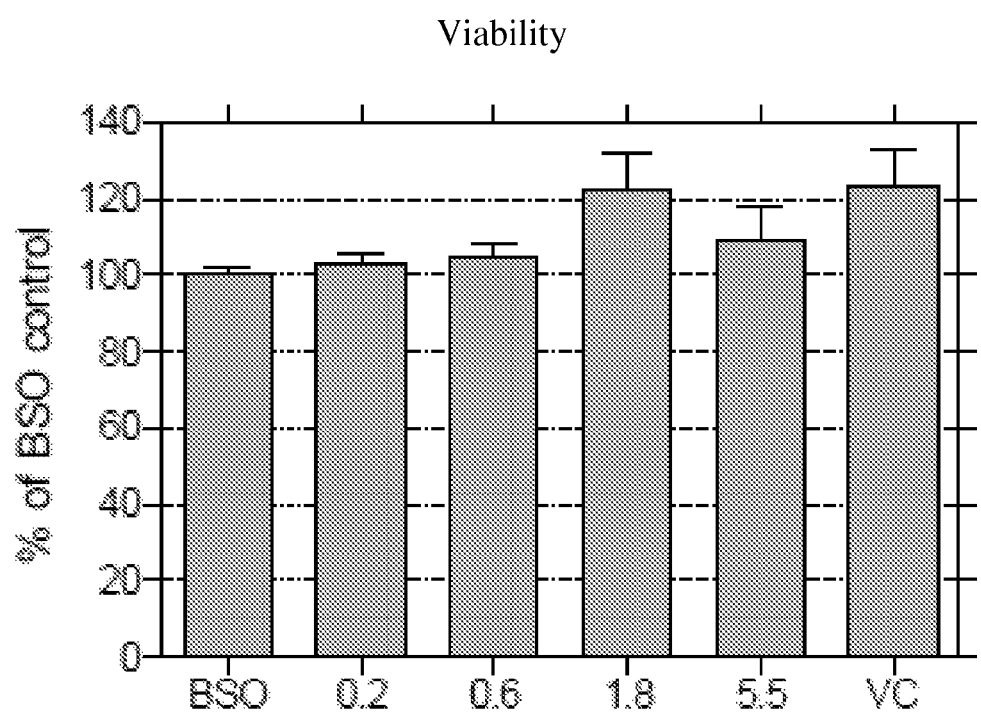

EXAMPLE. Tetrindole is diluted in DMSO. One vial is thawed and administered 2 and 24 hours before BSO treatment, at concentrations 0.2 µM, 0.6 µM, 1.8 µM and 5.5 µM. Apoptosis, toxicity and viability rate of cells are determined using the ApoTox-Glo-Kit (Promega). Human primary fibroblasts from patients suffering from LHON are used. Three independent experiments in four technical replicates are performed for all groups. The results are shown in FIGS. 4A and 4B. Graphs represent apoptosis and viability effect of tetrindole (addition 2 and 24 h before lesion) on LHON cells as % of the BSO lesion. The BSO lesion reduced cell viability by approximately 20% in LHON cells compared to VC. In the BSO lesion assay tetrindole showed a dose dependent protective trend (0.2 to 1.8 µM) on cell viability. At a concentration of 5.5 µM tetrindole induced an increase in apoptosis at early incubation times. The dose of 1.8 µM resulted in a 122% protective effect in relative cell viability ($p<0.05$). Statistically significant overall cytotoxicity over BSO control was not observed at any dose. Statistically significant improvement in apoptosis was not observed at any dose compared to the BSO group. However, there was not a statistically significant difference between the apoptosis observed at the 1.8 dose ($p=0.96$) or the highest dose of 5.5 ($p=0.52$), and that observed in the VC treatment group. Statistically significant improvement in viability was not observed at any dose compared to the BSO group. However, there was not a statistically significant difference between the viability observed at the 1.8 dose ($p=0.99$) or the highest dose of 5.5 (p=0.34), and that observed in the VC treatment group. Statistical significance is indicated by NS=not significant p>0.1, *=p<0.05, =p<0.01, *=p<0.001 as determined by One-Way ANOVA. Data are shown as group mean+/−SEM.

In each of the foregoing examples, the concentrations where the maximum protective effect was seen for the tested compounds have a similar ratio to the maximum plasma concentration ($C_{max}$) reported for the compounds in humans. For example, 16 µM corresponds to 15 times the $C_{max}$ of the maximum approved dose of pirlindole. It is therefore appreciated that for the structurally related compound tetrindole, the dose of 1.8 µM corresponding to the maximum protective effect will also correspond to 15 times the $C_{max}$ of that compound in humans.

EXAMPLE. Human FXN YAC transgenic mouse model YG8R of FRDA. This model contains 190+90 GAA repeat expansions (Al-Mandawi et al., GAA repeat instability in Friedreich ataxia YAC transgenic mice *Genomics* 84, 301-310 (2004)). The transgenic line exhibits intergenerational and age-related somatic instability of the GAA repeat, with the most prominent expansions occurring specifically in the cerebellum and DRG, as similarly seen in human FRDA autopsy tissues. By cross breeding the FXN YAC transgenic mice with heterozygous Fxn knockout mice, it was discovered herein that the YG8 transgene was able to successfully rescue the homozygous Fxn knockout embryonic lethality and that the rescue mice exhibit a similar FRDA-like phenotype (Al-Mandawi et al., GAA repeat expansion mutation mouse models of Friedreich ataxia exhibit oxidative stress leading to progressive neuronal and cardiac pathology *Genomics* 88, 580-590 (2006)). In particular, compared with wild-type or Y47 rescue (Y47R) control mice, decreased FXN mRNA and frataxin expression, decreased coordination ability (as determined by rotarod testing) and locomotor activity, decreased aconitase activity, oxidative stress (increased protein oxidation and lipid peroxidation), histopathology in DRG large sensory neurons and axons (vacuole formation and demyelination) and iron accumulation in the heart were each detected. The YG8 transgene expresses less FXN mRNA and frataxin than the YG22 transgene (Al-Mandawi et al., The Friedreich ataxia GAA repeat expansion mutation induces comparable epigenetic changes in human and transgenic mouse brain and heart tissues *Hum Mol Genet* 17, 735-746 (2008)), and YG8 rescue mice (YG8R) have a reduced rotarod coordination performance compared with YG22 rescue mice (YG22R). Though both models may be used, it is appreciated that the YG8R mice may be the preferred FRDA model.

EXAMPLE. Human FXN YAC transgenic mouse model YG22R of FRDA. This model contains 190 GAA repeat expansions (Al-Mandawi et al., GAA repeat instability in Friedreich ataxia YAC transgenic mice *Genomics* 84, 301-310 (2004)). The transgenic line exhibits intergenerational and age-related somatic instability of the GAA repeat, with the most prominent expansions occurring specifically in the cerebellum and DRG, as similarly seen in human FRDA autopsy tissues. By cross breeding the FXN YAC transgenic mice with heterozygous Fxn knockout mice, it was discovered herein that the YG22 transgene was able to successfully rescue the homozygous Fxn knockout embryonic lethality and that the rescue mice exhibit a similar FRDA-like phenotype (Al-Mandawi et al., GAA repeat expansion mutation mouse models of Friedreich ataxia exhibit oxidative stress leading to progressive neuronal and cardiac pathology *Genomics* 88, 580-590 (2006)). In particular, compared with wild-type or Y47 rescue (Y47R) control mice, decreased FXN mRNA and frataxin expression, decreased coordination ability (as determined by rotarod testing) and locomotor activity, decreased aconitase activity, oxidative stress (increased protein oxidation and lipid peroxidation), histopathology in DRG large sensory neurons and axons (vacuole formation and demyelination) and iron accumulation in the heart were each detected. The YG8 transgene expresses less FXN mRNA and frataxin than the YG22 transgene (Al-Mandawi et al., The Friedreich ataxia GAA repeat expansion mutation induces comparable epigenetic changes in human and transgenic mouse brain and heart tissues *Hum Mol Genet* 17, 735-746 (2008)), and YG8 rescue mice (YG8R) have a reduced rotarod coordination performance compared with YG22 rescue mice (YG22R). Though both models may be used, it is appreciated that the YG8R mice may be the preferred FRDA model.

EXAMPLE. Animals are evaluated for 4 months to detect the long-term beneficial effect of test compounds on the neurobehavioural, cellular and molecular pathological phenotype of YG8R FRDA mice. Illustratively, two doses of pirlindole (10 mg/kg and 30 mg/kg) and two doses of tetrindole (7 mg/kg and 20 mg/kg), are be orally administered in drinking water to groups of YG8R FRDA mice (GAA-FXN$^+$/Fxn$^{-/-}$), and compared vehicle-only treatment in as separate group of YG8R mice as a negative control. Optionally, idebenone (10 mg/kg) may be used as a positive control in a separate group of YG8R mice. Vehicle is also optionally administered to one group of Y47R mice (normal GAA-FXN$^+$/Fxn$^{-/-}$) as a non-disease control group. Each group consists of 10 age- and sex-matched young adult mice.

Phenotype analysis of all treated mice is performed throughout and subsequent to the period of drug administration. Mice are weighed at monthly intervals throughout the trial period as a measure of general health. Rotarod coordination and locomotor activity functional tests are performed on each group of mice at monthly intervals to determine any changes in neurobehavioural functioning. Illustratively, rotarod analysis is performed using an Ugo-Basille 7650 accelerating rotarod treadmill apparatus. Mice are placed on the rotarod and four trials are performed with the speed of the rotation gradually increasing from 4-40 rpm over a period of approximately 5 minutes. A period of 10 minutes rest is given between each trial. The time that it takes for each mouse to fall from the cylinder will be noted and an average latency to fall will be calculated for each group of mice. Differences between rotarod performances of the drug treated versus vehicle groups throughout the time course of the trial are statistically analysed by ANOVA with repeated measures and with a significance level set at 0.05. Illustratively, locomotor activity is assessed by placing the mice in a gridded open-field perspex box and the ambulatory distance, average speed, jump counts and vertical counts of the mouse over a period of 2 minutes are recorded by beam breakers positioned around the perspex box. Differences between locomotor activities of the drug treated versus vehicle groups is assessed by ANOVA with repeated measures and with a significance level set at 0.05.

Following the 4-month evaluation period, mice are sacrificed to obtain tissues for DNA, RNA, protein, lipid and biochemical enzyme activity experiments. Studies focus on the use of brain as a CNS tissue and heart as a non-CNS tissue. The GAA repeat expansion mutation within intron 1 of the FXN gene is evaluated to determine to what degree the mutation shows an age-related somatic instability. DNA is isolated from tissues and the FXN GAA repeat expansion is amplified by PCR using standard GAA-F and GAA-R primers (Campuzano et al., Friedreich's ataxia: autosomal recessive disease caused by an intronic GAA triplet repeat expansion *Science* 271:1423-1427 (1996)) FXN mRNA levels are determined by qRT-PCR. Total RNA is isolated from cells with Trizol and levels of transgenic FXN expression is assessed by qRT-PCR using SYBR® Green (Applied Biosystems) and human FXN-specific primers run on an ABI7900HT Fast Real-Time PCR System. Frataxin protein levels are determined by isolation of protein lysates from cells, followed by quantification using the MitoSciences frataxin dipstick assay kit. Protein lysates are also used to determine protein oxidation using the Oxyblot Protein Oxidation Detection Kit (Chemicon). Lipid peroxidation of tissues is assessed by determining the levels of MDA using the TBARS assay. The earliest known disease effect of frataxin deficiency is damage to the FeS cluster proteins, such as aconitase. Therefore, whole cell lysate aconitase enzyme activities can be optionally determined using the Aconitase Assay Kit (Cayman) and xMark microplate spectrophotometer (Biorad), normalising for mitochondrial content by measuring citrate synthase (CS) activity with the Citrate Synthase Activity Kit (Sigma). The results from the drug-treated versus placebo-treated FRDA mice are statistically analysed by ANOVA or the student's t test with a significance level set at 0.05.

EXAMPLE. Primary fibroblast and neuronal stem cell (NSC) cultures from the YG8R FRDA mouse model. The cell cultures are used as a rapid means to test the effectiveness of potential therapies before proceeding to longer-term FRDA mouse model investigations. A parallel assay using YG22R NSCs may be used. A conventional cell viability-based screening assay that demonstrates selective susceptibility of YG8R FRDA mouse cells, compared with wild-type mouse cells or Y47R control mouse cells, to an oxidative stress insult (100 µg/ml ferrous ammonium citrate (FAC) and 1 mM BSO for 48 hours) is performed.

YG8R fibroblasts and NSCs are treated with increasing concentrations of test compound, and a vehicle-only negative control. Optionally, YG8R fibroblasts and NSCs are treated with a positive control compound, such as 1 µM idebenone. Two hours after the initial treatment, cells are lesioned with 100 µM/mL FAC and 1 mM BSO for 48 hours. Cell viability is then determined using Presto Blue Cell Viability Reagent (Life Technologies) for 24 hours and subsequent colorimetric spectrophotometry. Both pirlindole and tetrindole significantly protect FRDA mouse fibroblasts against the oxidative stress insult. Treatment of fibroblasts with 16 µM pirlindole restored the vehicle-treated FAC/BSO cell viability value of 26% to a value of 67% ($p<0.001$), relative to the vehicle treated non-insulted cell value as 100%. Similarly, 1.8 µM tetrindole restored the vehicle-treated FAC/BSO cell viability value of 26% to a value of 53% ($p<0.001$), relative to the vehicle treated non-insulted cell value as 100%.

Both pirlindole and tetrindole significantly protect FRDA NSCs against the oxidative stress insult. Treatment of NSCs with 5.5 µM pirlindole restored the vehicle-treated FAC/BSO cell viability value of 19% to a value of 41% ($p<0.001$), relative to the vehicle treated non-insulted cell value as 100%. Similarly, 1.8 µM tetrindole restored the vehicle-treated FAC/BSO cell viability value of 19% to a value of 40% ($p<0.001$), relative to the vehicle treated non-insulted cell value as 100%.

EXAMPLE. Evaluation of anti-inflammatory and direct protection mode of action. Compounds described herein are evaluated in a standard MOG-induced Experimental Allergic Encephalomyelitis (MOG-EAE) mouse model of neurodegeneration to determine whether the compounds protect neurons directly, or via an indirect anti-inflammatory mode of action. EAE is induced in C57BL/6 mice by the single subcutaneous injection of MOG emulsified in Complete Freund's Adjuvant (CFA) on study days 0 and 6, followed by intraperitoneal supplemental immunostimulation with Pertussis Toxin (PT) carried out once at the time of EAE induction and once again 48 hours later. Test animals are observed for 35 days. Histology samples are harvested from the spinal cords of the animals on day 35 and are stained with Hematoxylin & Eosin (H&E). Analysis of the samples comprises two parameters: a) The Severity Score which refers mainly to infiltration by inflammatory cells and b) White Matter Damage (WMD), which refers mainly to axonal degeneration.

The Severity Score for the pirlindole 30 mg/kg treatment group was 2.7±1.29, compared to the positive control (dexamethasone) treatment group of 1.45±1.09, and vehicle only treatment group of 2.85±0.66. Dexamethasone is reported to reduce severity score via its anti inflammatory effects. Thus, the data demonstrate that the compounds described herein do not protect neurons via an anti-inflammatory mode of action. The WMD percentage for the pirlindole 30 mg/kg treatment group was 41±44.1, compared to the positive control treatment group of 24.4±33.3, and vehicle only treatment group of 74.2±26.1. The date support the conclusion that the compounds described herein have a significant direct protective effect ($p<0.05$). It is understood that the murine 30 mg/kg dose of pirlindole corresponds to about 2.4 mg/kg in humans, according to standard conversion methods. This 2.4 mg/kg dose is within the clinically approved range (up to 6 mg/kg).

EXAMPLE. Bioavailability, pharmacokinetics (PK), and toxicity.

Pirlindole exerts an inhibitory effect on the reuptake of noradrenaline and 5-hydroxytryptamine, while it has no effect on the dopaminergic and cholinergic systems. It has an absolute bioavailability of 20-30%, while the oral $T_{max}$ varies between approximately 2 and 6 hours in the rat, and approximately 1 and 2 hours in the dog. In the rat there are two phases of elimination (approximately 8 h and 35-70 h), while in the dog there are three phases of elimination (approximately 1.5 h, 11 h and 185 h). Pirlindole is metabolized. For example, the rat eliminates mainly unconjugated products while the dog eliminates mostly conjugated products. With regard to chronic administration, a pharmacokinetic study has been conducted in male and female dogs after repeated administration of three different dose levels p.o. for one year. The blood levels of pirlindole were strictly dose-dependent. Kinetic differences between males and females were not observed. In rats, after oral and i.p. administration, pirlindole shows good blood brain barrier (BBB) penetration, and showed a $C_{max}$ in the brain within approx 2 h; it was also distributed in the lungs, liver, kidneys, spleen and various glands (but only transiently in bone marrow). Pirlindole was eliminated 40-60% within 24 h, and 80-85% after 48 h.

The $LD_{50}$ after single dose oral administration is approximately 400 to 1000 mg/kg in mice and 2000 to 5000 mg/kg in rats. $LD^{50}$ after single dose i.v. administration is approximately 70-80 mg/kg in mice and 80 mg/kg in rats. The maximal non-lethal dose is approximately 300 mg/kg p.o. in the mouse. These doses, and their human equivalent doses, exceed the therapeutic doses described herein, and provide a sufficient therapeutic window.

What is claimed is:

1. A method for treating a mitochondrial disease in a patient, the method comprising the step of administering a therapeutically effective amount of one or more compounds of the formulae:

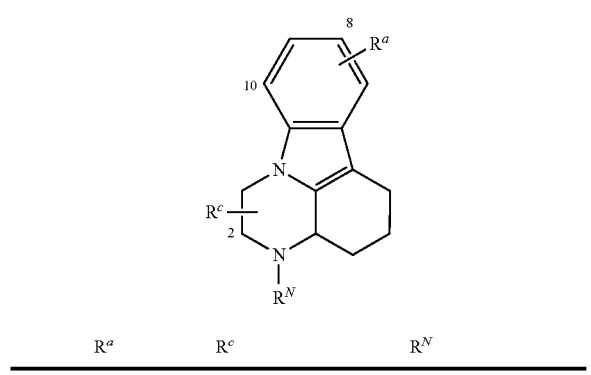

| $R^a$ | $R^c$ | $R^N$ |
|---|---|---|
| 8-OMe | H | Me |
| 8-cyclohexyl | H | H |
| 8-Me | H | $Me_2(CH_2)_4NHCH_2CH(OH)CH_2$ |
| 8-cyclohexyl | H | 3,4,5-trimethoxybenzoyl |
| 8-Br | H | n-Bu |
| 8-Me | H | $CF_3(CF_2)_3C(O)$ |
| H | H | $NH_2CH_2CH_2$ |
| 8-(4-methoxyphenyl) | H | H |
| 8-Me | H | 3-methyl-1-piperidinyl-C(O)CH$_2$ |
| 8-cyclododecyl | H | H |
| 8-Me | H | Me |
| 8-cyclohexyl | H | PhCH=CHCH=NNHC(O)CH$_3$ |
| 8-Me | H | 4-methyl-1-piperazinyl-CH$_2$CH(OH)CH$_3$ |
| 8-Me | H | 4-(3,4-dimethoxyphenyl)thiazol-2-yl |
| 8-F | H | H |
| 8-cyclohexyl | H | 1-methyl-3-nitro-1H-1,2,4-triazol-5-yl |
| 8-(adamant-1-yl) | H | H |
| 8-Me | H | piperidin-1-yl-CH(OH)CH$_2$ |
| 8-CO$_2$Et | H | H |
| H | 2-Ph | H |
| 8-cyclohexyl | H | Et$_2$NCH$_2$C(O) |
| 6,8-dimethyl | H | H |
| 8-Me | H | 4-ethylpiperazin-1-yl-CH$_2$CH(OH)CH$_2$ |
| 8-Me | H | NCCH$_2$ |
| 8-Me | H | NH$_2$CH$_2$CH$_2$ |
| 8-cyclohexyl | H | Et$_2$NCH$_2$CH$_2$ |
| 8-Me | H | NH$_2$C(O)CH$_2$CH$_2$ |
| 8-Me | H | CH$_3$C(O)CH$_2$ |
| 8-Me | H | 2-fluorobenzoyl |
| 8-OAc | H | H |
| 8-Me | H | (i-Pr)$_2$NCH$_2$CH$_2$ |
| 8-C(O)NHNH$_2$ | H | H |

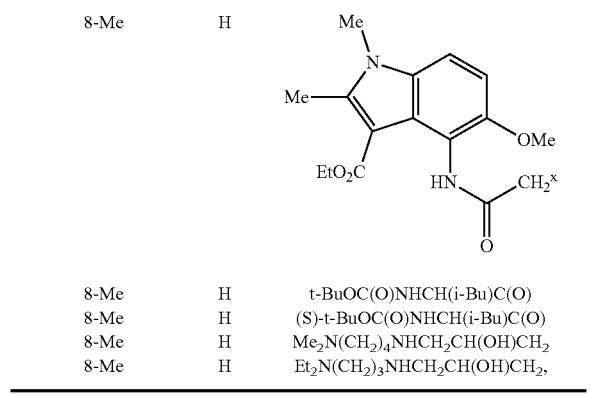

| 8-Me | H | t-BuOC(O)NHCH(i-Bu)C(O) |
| 8-Me | H | (S)-t-BuOC(O)NHCH(i-Bu)C(O) |
| 8-Me | H | Me$_2$N(CH$_2$)$_4$NHCH$_2$CH(OH)CH$_2$ |
| 8-Me | H | Et$_2$N(CH$_2$)$_3$NHCH$_2$CH(OH)CH$_2$, |

| $R^a$ | $R^c$ | $R^d$ | $R^N$ |
|---|---|---|---|
| 9-EtO | H | H | Me |
| 9-MeO | H | H | H |
| 9-MeO | H | H | n-propyl |
| 9-MeO | H | H | Me |
| 9-MeO | H | H | benzyl |
| H | H | H | Me |
| 9-F | H | H | Me |
| 9-MeO | H | H | cyclohexyl |
| 9-cyclohexyl | H | H | Me |
| 9-Me | H | H | Me |
| 9-hydroxy | H | H | Me |
| 7-MeO | H | H | Me |
| H | H | H | Et |
| 9-cyclohexyl | H | H | H |
| 9-n-PrO | H | H | Me |
| 8-MeO | H | H | Me |
| 9-benzyloxy | H | H | Me |
| H | 5-Me | H | Me |

| $R^a$ | $R^c$ | $R^d$ | $R^N$ |
|---|---|---|---|
| 9-EtO | H | H | Me |
| 9-MeO | H | H | H |
| 9-MeO | H | H | n-propyl |
| 9-MeO | H | H | Me |
| 9-MeO | H | H | benzyl |
| H | H | H | Me |
| 9-F | H | H | Me |
| 9-MeO | H | H | cyclohexyl |
| 9-cyclohexyl | H | H | Me |
| 9-Me | H | H | Me |
| 9-hydroxy | H | H | Me |
| 7-MeO | H | H | Me |
| H | H | H | Et |
| 9-cyclohexyl | H | H | H |
| 9-n-PrO | H | H | Me |
| 8-MeO | H | H | Me |

-continued

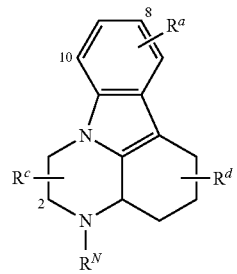

| $R^a$ | $R^c$ | $R^d$ | $R^N$ |
|---|---|---|---|
| 9-benzyloxy | H | H | Me |
| H | 5-Me | H | Me, | or

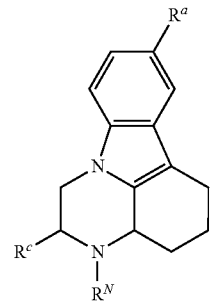

| $R^a$ | $R^c$ | $R^d$ | $R^N$ |
|---|---|---|---|
| 9-EtO | H | H | Me |
| 9-MeO | H | H | H |
| 9-MeO | H | H | n-propyl |
| 9-MeO | H | H | Me |
| 9-MeO | H | H | benzyl |
| H | H | H | Me |
| 9-F | H | H | Me |
| 9-MeO | H | H | cyclohexyl |
| 9-cyclohexyl | H | H | Me |
| 9-Me | H | H | Me |
| 9-hydroxy | H | H | Me |
| 7-MeO | H | H | Me |
| H | H | H | Et |
| 9-cyclohexyl | H | H | H |
| 9-n-PrO | H | H | Me |
| 8-MeO | H | H | Me |
| 9-benzyloxy | H | H | Me |
| H | 5-Me | H | Me | or pharmaceutically acceptable salts thereof, or a combination thereof to the patient, where the mitochondrial disease is selected from the group consisting of FRDA, LHON, DAD, Leigh's disease, NARP, MNGIE, MERRF, and MELAS.

2. The method of claim 1 wherein the mitochondrial disease is FRDA.

3. The method of claim 1 wherein the mitochondrial disease is LHON.

4. The method of claim 1 wherein at least one of the compounds is of the formula

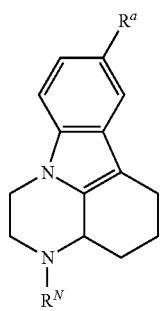

(I)

or a pharmaceutically acceptable salt thereof.

5. The method of claim 1 wherein at least one of the compounds is of the formula (Ia)

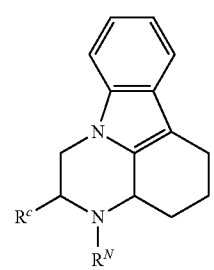

or a pharmaceutically acceptable salt thereof.

6. The method of claim 1 wherein at least one of the compounds is of the formula (Ib)

or a pharmaceutically acceptable salt thereof.

7. The method of claim 1 wherein at least one of the compounds is of the formula (Ic)

or a pharmaceutically acceptable salt thereof.

8. The method of claim 4 wherein $R^a$ is methyl.

9. The method of claim 4 wherein $R^a$ is methoxy.

10. The method of claim 4 wherein $R^c$ is hydrogen.

11. The method of claim 4 wherein $R^d$ is hydrogen.

12. The method of claim 4 wherein $R^N$ is hydrogen.

13. The method of claim 4 wherein $R^N$ is methyl.

14. The method of claim 1 wherein the compound is tetrindole or metralindole, or a pharmaceutically acceptable salt thereof.

15. The method of claim 2 wherein the compound is tetrindole or metralindole, or a pharmaceutically acceptable salt thereof.

16. The method of claim 3 wherein the compound is tetrindole or metralindole, or a pharmaceutically acceptable salt thereof.

* * * * *